US012318380B2

(12) United States Patent
Prisinzano et al.

(10) Patent No.: US 12,318,380 B2
(45) Date of Patent: *Jun. 3, 2025

(54) TREATMENT OF DEMYELINATING DISEASES

(71) Applicants: Victoria Link Ltd., Wellington (NZ); University of Kansas, Lawrence, KS (US)

(72) Inventors: Thomas Edward Prisinzano, Lawrence, KS (US); Bronwyn Maree Kivell, Wellington (NZ); Anne Camille La Flamme, Wellington (NZ)

(73) Assignees: Victoria Link Ltd., Wellington (NZ); University of Kansas, Lawrence, KS (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/957,350

(22) Filed: Sep. 30, 2022

(65) Prior Publication Data

US 2023/0096920 A1 Mar. 30, 2023

Related U.S. Application Data

(63) Continuation of application No. 16/978,542, filed as application No. PCT/IB2019/051870 on Mar. 7, 2019, now abandoned.

(30) Foreign Application Priority Data

Mar. 8, 2018 (AU) ................................ 2018900754

(51) Int. Cl.
*A61K 31/485* (2006.01)
*A61P 25/28* (2006.01)

(52) U.S. Cl.
CPC ............ *A61K 31/485* (2013.01); *A61P 25/28* (2018.01)

(58) Field of Classification Search
CPC ........ A61K 31/485; A61P 25/02; A61P 25/28; A61P 25/00
USPC ........................................................ 514/282
See application file for complete search history.

(56) References Cited

U.S. PATENT DOCUMENTS

| | | | |
|---|---|---|---|
| 4,994,466 A | 2/1991 | Sherman et al. | |
| 5,849,731 A | 12/1998 | Nagase et al. | |
| 6,174,891 B1 | 1/2001 | Nagase et al. | |
| 6,372,755 B2 | 4/2002 | Hanamura et al. | |
| 6,440,987 B1 | 8/2002 | Nagase et al. | |
| 6,770,654 B2 | 8/2004 | Sakami et al. | |
| 6,984,493 B1 | 1/2006 | Kumagai et al. | |
| 7,320,984 B2 | 1/2008 | Izumimoto et al. | |
| 7,718,664 B2 | 5/2010 | Izumimoto et al. | |
| 7,803,942 B2 | 9/2010 | Wakita et al. | |
| 8,058,286 B2 | 11/2011 | Kawai et al. | |
| 8,106,065 B2 | 1/2012 | Izumimoto et al. | |
| 8,338,442 B2 | 12/2012 | Kumagi et al. | |
| 8,420,662 B2 | 4/2013 | Takaki et al. | |
| 8,470,845 B2 | 6/2013 | Izumimoto | |
| 8,637,539 B2 | 1/2014 | Nagase et al. | |
| 8,715,730 B2 | 5/2014 | Takaki et al. | |
| 8,796,301 B2 | 8/2014 | Ikeda et al. | |
| 8,829,019 B2 | 9/2014 | Ohta et al. | |
| 9,006,262 B2 | 4/2015 | Suzuki et al. | |
| 9,051,335 B2 | 6/2015 | Umeuchi et al. | |
| 9,592,288 B2 | 3/2017 | Schultz et al. | |
| 10,131,672 B2 | 11/2018 | Kobayashi et al. | |
| 11,324,742 B2 * | 5/2022 | Prisinzano .............. | A61P 25/02 |
| 2006/0069086 A1 | 3/2006 | Michalow | |
| 2010/0222309 A1 | 9/2010 | Ona et al. | |
| 2012/0114752 A1 | 5/2012 | Ohta et al. | |
| 2014/0038949 A1 | 2/2014 | Schultz et al. | |
| 2015/0316539 A1 | 11/2015 | Chan et al. | |
| 2017/0136029 A1 | 5/2017 | Schultz et al. | |
| 2021/0015813 A1 | 1/2021 | Kivell et al. | |
| 2021/0023074 A1 | 1/2021 | Kivell et al. | |
| 2021/0069179 A1 | 3/2021 | Prisinzano et al. | |

FOREIGN PATENT DOCUMENTS

| | | |
|---|---|---|
| CN | 102993125 A | 3/2013 |
| CN | 105462930 A | 4/2016 |
| EP | 3603643 | 5/2020 |
| JP | 2000053572 A | 2/2000 |
| JP | 3123080 B2 | 1/2001 |
| JP | 2001163784 A | 6/2001 |
| JP | 2002332284 A | 11/2004 |
| JP | 4292738 B2 | 7/2009 |
| JP | 4311369 B2 | 8/2009 |
| JP | 2009196933 A | 9/2009 |

(Continued)

OTHER PUBLICATIONS

Agrawal, "Low dose naltrexone therapy in multiple sclerosis," Medical Hypotheses, Jan. 1, 2005, 64(4):721-4.
Bannerman et al., "Motor neuron pathology in experimental autoimmune encephalomyelitis: studies in THY1-YFP transgenic mice," Brain, Aug. 1, 2005, 128(8):1877-86.
Berger, "Functional improvement and symptom management in multiple sclerosis: clinical efficacy of current therapies," American Journal of Managed Care, May 1, 2011, 17(5):S146, 9 pages.
Borniger et al., "Enhancing Remyelination through a Novel Opioid-Receptor Pathway," Journal of Neuroscience, Nov. 23, 2016, 36(47):11831-3.
Brown et al., "Low-dose naltrexone for disease prevention and quality of life," Medical Hypotheses, Mar. 1, 2009, 72(3):333-7.

(Continued)

*Primary Examiner* — Charanjit Aulakh
(74) *Attorney, Agent, or Firm* — Fish & Richardson P.C.

(57) ABSTRACT

The present invention relates generally to methods of using nalfurafine for treating and/or preventing demyelinating disease in a subject, and in particular for treating and/or preventing multiple sclerosis (MS). Also disclosed is nalfurafine for use in treating and/or preventing MS as well as pharmaceutical compositions and unit dosage forms comprising nalfurafine for use for treating and/or preventing demyelinating disease in a subject, and in particular for treating and/or preventing MS.

15 Claims, 24 Drawing Sheets

(56) References Cited

FOREIGN PATENT DOCUMENTS

| | | |
|---|---|---|
| JP | 4370683 B2 | 11/2009 |
| JP | 4453254 B2 | 4/2010 |
| JP | 2011074018 A | 4/2011 |
| JP | 4706636 B2 | 6/2011 |
| JP | 4867123 B2 | 2/2012 |
| JP | 4882744 B2 | 2/2012 |
| JP | 4957489 B2 | 6/2012 |
| JP | 5076498 B2 | 11/2012 |
| JP | 5119925 B2 | 1/2013 |
| JP | 5163127 B2 | 3/2013 |
| JP | 5251870 B2 | 7/2013 |
| JP | 5578199 B2 | 8/2014 |
| JP | 5613417 B2 | 10/2014 |
| JP | 5696742 B2 | 4/2015 |
| JP | 2015168630 A | 9/2015 |
| JP | 5867081 B2 | 2/2016 |
| JP | 5929753 B2 | 6/2016 |
| JP | 5971272 B2 | 8/2016 |
| JP | 2016155794 A | 9/2016 |
| JP | 2018048093 A | 3/2018 |
| WO | WO 1993015081 A1 | 8/1993 |
| WO | WO 2008024490 | 2/2008 |
| WO | WO 2013112859 A1 | 8/2013 |
| WO | WO 2013184794 A3 | 1/2014 |
| WO | WO 2016195057 | 12/2016 |
| WO | WO 2017049252 A1 | 3/2017 |
| WO | WO 2017220431 A1 | 12/2017 |
| WO | WO 2019171332 | 9/2019 |
| WO | WO 2019171333 | 9/2019 |

OTHER PUBLICATIONS

Bruchas et al., "Kinase cascades and ligand-directed signaling at the kappa opioid receptor," Psychopharmacology, Jun. 2010, 210(2):137-47.

Chavoustie, "Tests for Multiple Sclerosis," Healthline, Feb. 2018, 7 pages.

Chiba et al., "Fingolimod (FTY720), sphingosine 1-phosphate receptor modulator, shows superior efficacy as compared with interferon-β in mouse experimental autoimmune encephalomyelitis," International Immunopharmacology, Mar. 1, 2011, 11(3):366-72.

Cree et al., "Pilot trial of low-dose naltrexone and quality of life in multiple sclerosis," Annals of Neurology, Aug. 2010, 68(2):145-50.

Dogra et al., "Biased agonism at kappa opioid receptors: Implication in pain and mood disorders," European Journal of Pharmacology, Sep. 15, 2015, 763:184-90.

Du et al., "G protein-coupled receptors as therapeutic targets for multiple sclerosis," Cell Research, Jul. 2012, 22(7):1108-28.

Du et al., "Kappa opioid receptor activation alleviates experimental autoimmune encephalomyelitis and promotes oligodendrocyte-mediated remyelination," Nature Communications, Apr. 4, 2016, 7:11120, 10 pages.

Eschenroeder et al., "Oligodendrocyte responses to buprenorphine uncover novel and opposing roles of μ-opioid-and nociceptin/orphanin FQ receptors in cell development: Implications for drug addiction treatment during pregnancy," Glia, Jan. 2012, 60(1):125-36.

Fantegrossi et al., "Kappa-opioid receptor-mediated effects of the plant-derived hallucinogen, salvinorin A, on inverted screen performance in the mouse," Behavioural Pharmacology, Dec. 1, 2005, 16(8):627-33.

Fujij et al., "Opioid kappa receptor selective agonist TRK-820 (nalfurafine hydrochloride)," Pharmacology, ed G Luca, London InTech Mar. 14, 2012, 81-98.

Hahn et al., "Mu and kappa opioids modulate mouse embryonic stem cell-derived neural progenitor differentiation via MAP kinases," Journal of Neurochemistry, Mar. 2010, 112(6):1431-41.

Harlow et al., "Remyelination therapy in multiple sclerosis," Frontiers in Neurology, Dec. 10, 2015, 6:257, 13 pages.

Hubler et al., "Accumulation of 8, 9-unsaturated sterols drives oligodendrocyte formation and remyelination," Nature, Aug. 2018, 560(7718):372-6.

Inui, "Nalfurafine hydrochloride to treat pruritus: a review," Clinical, Cosmetic and Investigational Dermatology, May 11, 2015, 8:249-55.

Jamshidi et al., "Functional selectivity of kappa opioid receptor agonists in peripheral sensory neurons," Journal of Pharmacology and Experimental Therapeutics, Nov. 1, 2015, 355(2):174-82.

Kamimura et al., "Long-term efficacy and safety of nalfurafine hydrochloride on pruritus in chronic liver disease patients: Patient-reported outcome based analyses," PloS one, Jun. 12, 2017, 12(6):e0178991, 11 pages.

Klineova and Lublin (2018) Cold Spring Harb Perspect Med, doi: 10.1101/cshperspect.a028928.

Klineova et al., "Clinical course of multiple sclerosis," Cold Spring Harbor Perspectives in Medicine, Sep. 1, 2018, 8(9), 12 pages.

Kumagai et al., "Effect of a novel kappa-receptor agonist, nalfurafine hydrochloride, on severe itch in 337 haemodialysis patients: a Phase III, randomized, double-blind, placebo-controlled study," Nephrology Dialysis Transplantation, Apr. 1, 2010, 25(4):1251-7.

Kyle, "Functionally biased agonism of mu and kappa opioid receptors," Research and Development of Opioid-Related Ligands, American Chemical Society, May 2013, 177-97.

Le Gros, "Annual Report 2017," Malaghan Institute of Medical Research, 2017, 24 pages.

Li et al., "Low-dose naltrexone (LDN): A promising treatment in immune-related diseases and cancer therapy," International Immunopharmacology, Aug. 1, 2018, 61:178-84.

Liu et al., "In vivo brain GPCR signaling elucidated by phosphoproteomics," Science, Jun. 22, 2018, 360(6395), 12 pages.

Liu et al., "Phosphoproteomic approach for agonist-specific signaling in mouse brains: mTOR pathway is involved in κ opioid aversion," Neuropsychopharmacology, Apr. 2019, 44(5):939-49.

Ludwig et al., "Modulation of the OGF-OGFr pathway alters cytokine profiles in experimental autoimmune encephalomyelitis and multiple sclerosis," Experimental Biology and Medicine, Feb. 2018, 243(4):361-9.

Mei et al., "Identification of the kappa-opioid receptor as a therapeutic target for oligodendrocyte remyelination," Journal of Neuroscience, Jul. 27, 2016, 36(30):7925-35.

Mindur et al., "Early treatment with anti-VLA-4 mAb can prevent the infiltration and/or development of pathogenic CD11b+ CD4+ T cells in the CNS during progressive EAE," PloS one, Jun. 4, 2014, 9(6), 10 pages.

Münzel et al., "Promoting remyelination in multiple sclerosis—recent advances," Drugs, Dec. 2013, 73(18):2017-29.

Münzel, "Promoting remyelination in multiple sclerosis—recent advances," Drugs, Dec. 2013, 73(18):2017-29.

Nakao et al., "Nalfurafine hydrochloride, a selective κ opioid receptor agonist, has no reinforcing effect on intravenous self-administration in rhesus monkeys," Journal of Pharmacological Sciences, Jan. 1, 2016, 130(1):8-14.

Neurological Foundation, "Dec. 2016 research grant round recipients announced," retrieved Jul. 2, 2020 online at URL: <https://www.scoop.co.nz/stories/SC1612/S00034/december-2016-research-grant-round-recipients-announced.htm>, Dec. 14, 2016, 25 pages.

Ottervald et al., "Multiple sclerosis: Identification and clinical evaluation of novel CSF biomarkers," Journal of Proteomics, Apr. 18, 2010, 73(6):1117-32.

Paille et al., "Nalmefene: a new approach to the treatment of alcohol dependence," Substance Abuse and Rehabilitationm, Aug. 8, 2014, 5:87-94.

PCT International Preliminary Report on Patentability in International Appln. No. PCT/IB2019/051869, dated Sep. 8, 2020, 5 pages.

PCT International Preliminary Report on Patentability in International Appln. No. PCT/IB2019/051870, dated Sep. 8, 2020, 5 pages.

PCT International Search Report and Written Opinion in International Appln. No. PCT/IB2019/051869, dated May 1, 2019, 8 pages.

PCT International Search Report and Written Opinion in International Appln. No. PCT/IB2019/051870, dated May 1, 2019, 9 pages.

(56) References Cited

OTHER PUBLICATIONS

Persson et al., "Opioid-induced proliferation through the MAPK pathway in cultures of adult hippocampal progenitors," Molecular and Cellular Neuroscience, Jul. 1, 2003, 23(3):360-72.

Pradhan et al., "Ligand-directed signalling within the opioid receptor family," British Journal of Pharmacology, Nov. 2012, 167(5):960-9.

Rahn et al., "Prevention and diminished expression of experimental autoimmune encephalomyelitis by low dose naltrexone (LDN) or opioid growth factor (OGF) for an extended period: Therapeutic implications for multiple sclerosis," Brain Research, Mar. 24, 2011, 1381:243-53.

Raknes et al., "Low dose naltrexone in multiple sclerosis: Effects on medication use, A quasi-experimental study," PloS one, Nov. 3, 2017, 12(11):e0187423, 13 pages.

Schattauer et al., "Nalfurafine is a G-protein biased agonist having significantly greater bias at the human than rodent form of the kappa opioid receptor," Cellular Signalling, Apr. 1, 2017, 32:59-65.

Scoop News, "Dec. 2016 research grant round recipients announced," Dec. 14, 2016, retrieved Nov. 16, 2020 from URL <https://www.scoop.co.nz/stories/SC1612/S00034/december-2016-research-grant-round-recipients-announced.htm?from-mobile=bottom-link-01>, 13 pages.

Shang et al., "Opioid receptors: structural and mechanistic insights into pharmacology and signaling," European Journal of Pharmacology, Sep. 15, 2015, 763:206-13.

Turel et al., "Low dose naltrexone for treatment of multiple sclerosis: a retrospective chart review of safety and tolerability," Journal of Clinical Psychopharmacology, Oct. 1, 2015, 35(5):609-11.

Turner et al., "Reduction of inflammation and preservation of neurological function by anti-CD52 therapy in murine experimental autoimmune encephalomyelitis," Journal of Neuroimmunology, Aug. 15, 2015, 285:4-12.

Umeuchi et al., "Involvement of central μ-opioid system in the scratching behavior in mice, and the suppression of it by the activation of κ-opioid system," European Journal of Pharmacology, Sep. 5, 2003, 477(1):29-35.

U.S. Office Action in U.S. Appl. No. 16/936,975, dated Feb. 12, 2021, 27 pages.

U.S. Office Action in U.S. Appl. No. 16/978,542, dated Apr. 1, 2022, 23 pages.

Valentino et al., "Untangling the complexity of opioid receptor function," Neuropsychopharmacology, Dec. 2018, 43(13):2514-20.

Vestal-Laborde et al., "The opioid system and brain development; effects of methadone on the oligodendrocyte lineage and the early stages of myelination," Developmental Neuroscience, Aug. 2014, 36(5):409-21.

Weber et al., "B-cell activation influences T-cell polarization and outcome of anti-CD20 B-cell depletion in central nervous system autoimmunity," Annals of Neurology, Sep. 2010, 68(3):369-83.

Wijnands et al., "Five years before multiple sclerosis onset: phenotyping the prodrome," Multiple Sclerosis Journal, Jul. 2019, 25(8):1092-101.

Wikström et al., "κ-Opioid system in uremic pruritus: multicenter, randomized, double-blind, placebo-controlled clinical studies," Journal of the American Society of Nephrology, Dec. 1, 2005, 16(12):3742-7.

Yamamoto et al., "Paroxysmal itching in multiple sclerosis: a report of three cases," Journal of Neurology, Neurosurgery & Psychiatry, Jan. 1, 1981, 44(1):19-22.

\* cited by examiner

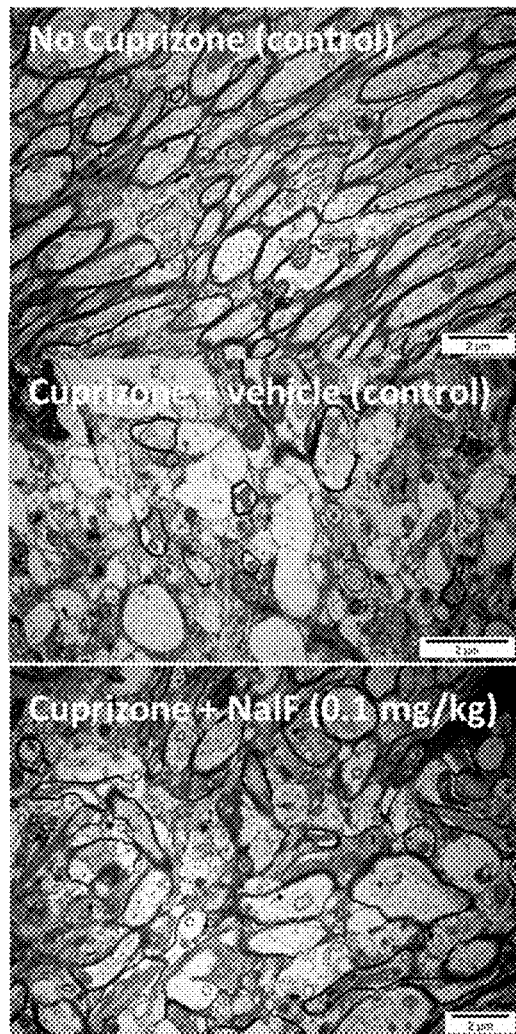
FIG. 9A
FIG. 9B
FIG. 9C
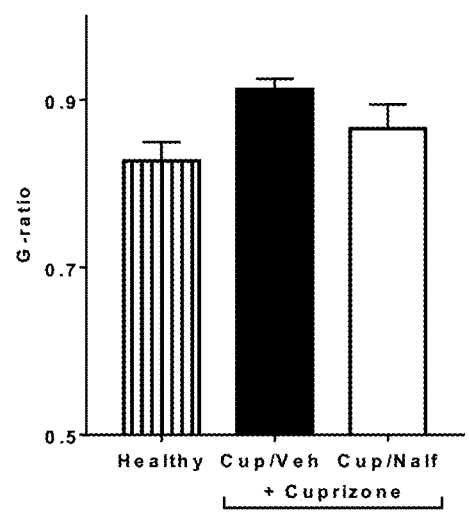
FIG. 9D

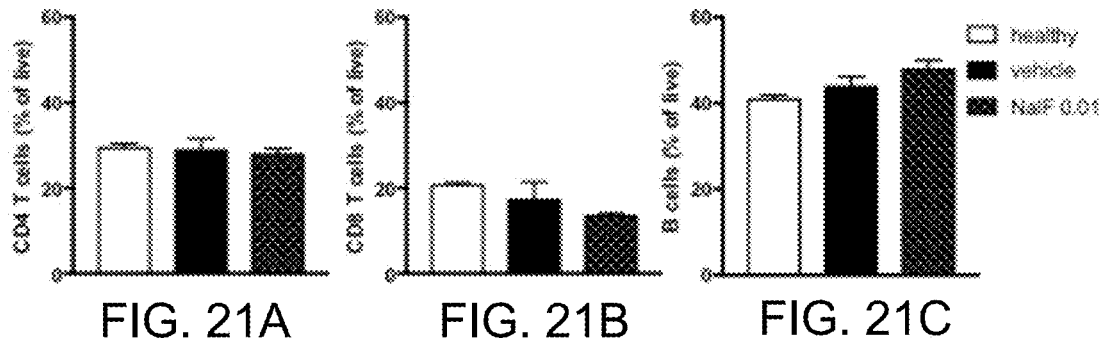
FIG. 21A  FIG. 21B  FIG. 21C
FIG. 22A  FIG. 22B
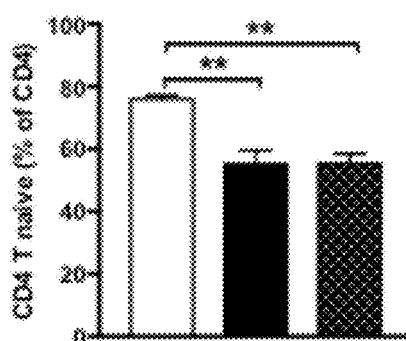 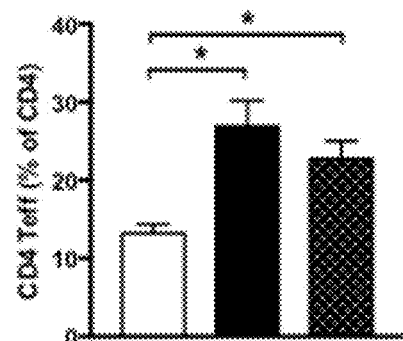
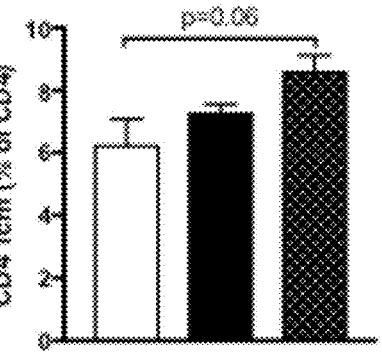 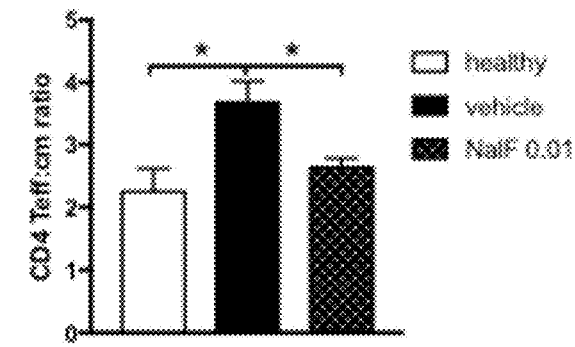
FIG. 22C  FIG. 22D Normal Cuprizone +Vehicle Cuprizone + U50,488

Cuprizone + NalF

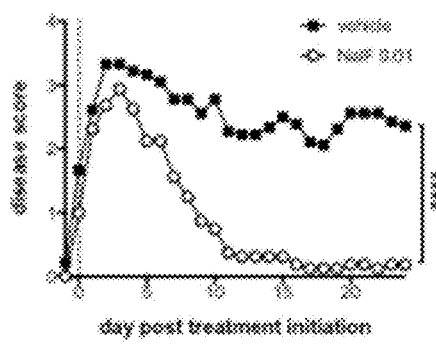
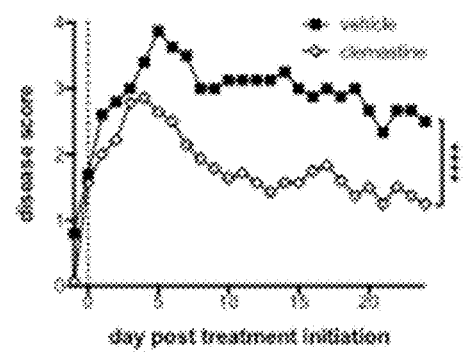
FIG. 30A  FIG. 30B
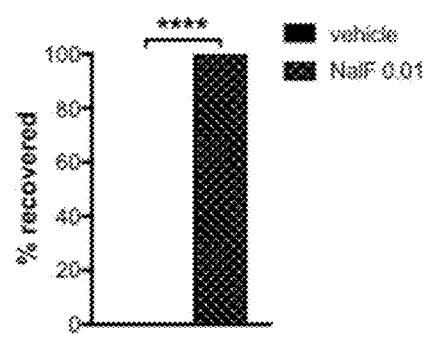
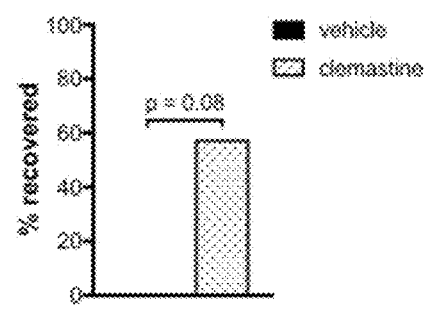
FIG. 31A-1  FIG. 31A-2
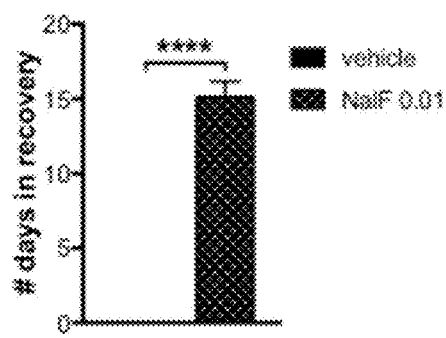
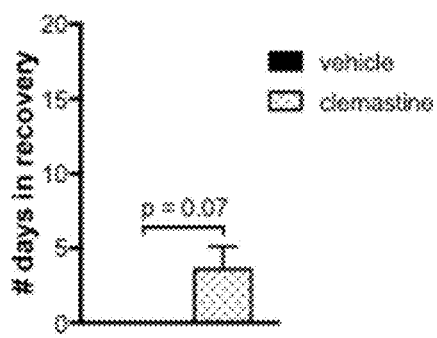
FIG. 31B-1  FIG. 31B-2

TREATMENT OF DEMYELINATING DISEASES

1. U.S. GOVERNMENT RIGHTS

This invention was made with government support under DA018151 awarded by the National Institutes of Health. The government has certain rights in the invention.

2. TECHNICAL FIELD

The disclosure relates generally to the use of nalfurafine (NaIF) in the prevention and treatment of demyelinating diseases, in particular, multiple sclerosis.

3. BACKGROUND

The myelin sheath covers important nerve fibres in the central and peripheral nervous system of mammals, helping to facilitate transmission of neural impulses. Diseases that affect myelin interrupt these nerve transmissions. The developing myelin sheath can be affected by congenital metabolic disorders such as phenylketonuria, Tay-Sachs disease, Niemann-Pick disease, Hurler's syndrome, and Krabbe's disease. Demyelination can also occur in adults as a result of injury, metabolic disorders, immune attack, ischemia and toxic agents.

Demyelination impairs conduction of signals to the affected nerves, causing deficiency of sensation, movement, cognition and other functions. Demyelination of the central nervous system is associated with multiple sclerosis (MS), Devic's disease, acute disseminated encephalomyelitis, adrenoleukodystrophy, leukoencephalopathy and Leber's optic atrophy. Demyelination of the peripheral nervous symptom gives rise to diseases such as Guillain-Barre syndrome, chronic inflammatory demyelinating polyneuropathy, Charcot Marie Tooth (CMT) disease and progressing inflammatory neuropathy.

Multiple sclerosis (MS) is the most well-known demyelination disease, affecting about 2.5 million people worldwide. Sufferers endure a range of symptoms including fatigue, vision problems, numbness, cognitive impairment, incontinence, poor balance and muscle weakness, ultimately leading to paralysis. MS can follow four major disease courses, each of which can be mild, moderate or severe:
1. Relapsing-Remitting MS (RRMS)—clearly defined attacks (flare-ups) of worsening neurological function followed by partial or complete remission
2. Primary-Progressive MS (PPMS)—slowly worsening neurological function at variable rates, with no distinct remission
3. Secondary-Progressing MS (SPMS)—an initial period of RRMS is followed by a steady worsening, with or without flare-ups and remissions
4. Progressive-Relapsing MS (PRMS)—steadily worsening neurological function with clear flare-ups and partial or no remission.

While there is no cure for MS, many FDA approved drugs such as beta-interferon and glatiramer acetate are used to reduce relapse rates and the formation of new lesions. Unfortunately, current treatments are not very successful in preventing the disability associated with MS and are more successful in treating RRMS than other types. For example, current drugs are unable to stop or reverse disease progression and disability. Clearly, alternative treatments for MS are needed.

It is therefore an object of the present invention to go at least some way towards meeting this need in the art, to provide products and methods useful in the treatment of the disability associated with MS and/or that are able to stop and/or reverse MS disease progression and disability and/or to at least to provide the public with a useful choice.

4. SUMMARY OF THE INVENTION

In one aspect the invention provides a pharmaceutical composition comprising nalfurafine and pharmaceutically acceptable excipients for treating a demyelinating disease in a subject in need thereof.

In one aspect the invention provides a pharmaceutical composition comprising nalfurafine and at least one pharmaceutically acceptable excipient for use for treating a demyelinating disease in a subject in need thereof.

In another aspect the invention provides unit dosage forms comprising about 0.01 to about 5 mg of nalfurafine and at least one pharmaceutically acceptable carrier or excipient. In one embodiment, the unit dosage form comprises 0.05 to about 2.0 mg of nalfurafine and at least one pharmaceutically acceptable carrier or excipient. In one embodiment the unit dosage form comprises about 0.15 to about 0.6 mg nalfurafine and at least one pharmaceutically acceptable carrier or excipient.

In another aspect the invention provides a method of treating a demyelinating disease in a subject in need thereof, comprising administering a therapeutically effective amount of nalfurafine to the subject.

In another aspect the invention provides a method of treating a demyelinating disease in a subject comprising identifying a subject who would benefit from a decreased level of demyelination and administering to the subject a therapeutically effective amount of an agent that decreases the level of demyelination in the subject relative to the level of demyelination before administering the agent, wherein the agent comprises nalfurafine.

In another aspect the invention provides a method of treating a demyelinating disease in a subject in need thereof, comprising administering to the subject a therapeutically effective amount of an agent that decreases the level of demyelination in the subject relative to the level of demyelination before administering the agent, wherein the agent comprises nalfurafine.

In another aspect the invention provides a method of increasing remyelination in a subject in need thereof, comprising administering a therapeutically effective amount of nalfurafine to the subject.

In another aspect the invention provides a method of increasing remyelination in a subject comprising identifying a subject who would benefit from an increased level of remyelination and administering to the subject a therapeutically effective amount of an agent that increases the level of remyelination in the subject relative to the level of remyelination before administering the agent, wherein the agent comprises nalfurafine.

In another aspect the invention provides a method of increasing remyelination in a subject in need thereof, comprising administering to the subject a therapeutically effective amount of an agent that increases the level of remyelination in the subject relative to the level of remyelination before administering the agent, wherein the agent comprises nalfurafine.

The invention also provides a use of nalfurafine in the manufacture of a medicament for treating a demyelinating disease in a subject in need thereof.

The invention also provides a use of nalfurafine in the manufacture of a medicament for increasing remyelination in a subject in need thereof.

The invention also provides nalfurafine for use for treating a demyelinating disease.

The invention also provides nalfurafine for use for increasing remyelination.

In one embodiment the disease is a demyelinating myelinoclastic disease.

In one embodiment the disease is a demyelinating leukodystrophic disease.

In one embodiment the demyelinating disease is a central nervous system demyelinating disease. In one embodiment the central nervous system demyelinating disease is selected from the group comprising MS (including clinically isolated syndrome; CIS), optic neuritis, Devic's disease, inflammatory demyelinating diseases, central nervous system neuropathies, myelopathies like Tabes dorsalis, leukoencephalopathies, leukodystrophies, or a combination thereof.

In one embodiment the demyelinating disease is MS.

In another embodiment the demyelinating disease is a peripheral nervous system demyelinating disease. In one embodiment the peripheral nervous system demyelinating disease is elected from the group comprising Guillain-Barre syndrome and its chronic counterpart, chronic inflammatory demyelinating polyneuropathy, anti-myelin associated glycoprotein (MAG) peripheral neuropathy, Charcot Marie Tooth (CMT) disease, copper deficiency and progressive inflammatory neuropathy.

In another aspect the invention provides a method of attenuating demyelination in a subject in need thereof, comprising administering a therapeutically effective amount of nalfurafine to the subject and thereby attenuating a level of demyelination in the subject relative to the level of demyelination when nalfurafine is not administered.

The invention also provides a use of nalfurafine in the manufacture of a medicament for attenuating demyelination in a subject in need thereof. In one embodiment, the subject is a human with MS The invention also provides nalfurafine for use for attenuating demyelination in a subject in need thereof.

In another aspect the invention provides a method of treating MS in a subject in need thereof, comprising administering a therapeutically effective amount of nalfurafine to the subject.

In another aspect the invention provides a method of treating MS in a subject in need thereof, comprising administering to the subject a therapeutically effective amount of an agent that decreases a level of demyelination in the subject relative to the level before administering the agent and/or that increases a level of remyelination in the subject relative to the level before administering the agent, wherein the agent comprises nalfurafine.

The invention also provides a use of nalfurafine in the manufacture of a medicament for treating MS in a subject in need thereof.

The invention also provides nalfurafine for use for treating MS in a subject in need thereof.

In one embodiment the subject has RRMS. In one embodiment the subject has PPMS. In one embodiment the subject has, or is diagnosed as having, SPMS. In one embodiment the subject has, or is diagnosed as having, PRMS. In one embodiment the subject has, or is diagnosed as having, Clinically Isolated Syndrome (CIS).

In one embodiment the treatment of MS results in one or more clinical outcomes when compared to subjects not treated with nalfurafine selected from the group consisting of:

(a) a decrease in MS disease progression;
(b) a decrease in MS disease severity;
(c) a decrease in nerve cell demyelination;
(d) a decrease in frequency or severity of relapsing MS attacks;
(e) a decrease in MS clinical symptoms;
(f) the healing of damaged nerve tissue (neuro-restoration);
(g) an increase in remyelination of demyelinated nerves in the central nervous system (neuro-restoration/protection);
(h) the protection of damaged nerve tissue from further disease activity (neuro-protection);
(i) the promotion of neuronal outgrowth (neuro-regeneration) in the central nervous system;
(j) a decrease in disability caused by MS;
(k) an improvement of nerve function; and
(l) an enhanced rate of remission.

In another embodiment the treatment of MS results in a reduction of one or more clinical symptoms of MS including, but not limited to loss of sensitivity or changes in sensation such as tingling, pins and needles or numbness, muscle weakness or paralysis of variable severity, very pronounced reflexes, muscle spasms, or difficulty in moving; difficulties with coordination and balance (ataxia); spasticity; problems with speech or swallowing, visual problems (nystagmus, optic neuritis or double vision), fatigue, acute or chronic pain, neuropathic pain, facial pain (trigeminal neuralgia), bladder and bowel difficulties, incontinence, reduced cognitive ability, depression, anxiety and other emotional abnormalities, sexual dysfunction, Uhthoff's phenomenon (a worsening of symptoms due to exposure to higher than usual temperatures), and Lhermitte's sign (an electrical sensation that runs down the back when bending the neck).

In one aspect the invention provides a method of accelerating remission from MS in a subject in need thereof, the method comprising administering a therapeutically effective amount of nalfurafine to the subject.

In one aspect the invention provides a method of accelerating remission from MS in a subject in need thereof, the method comprising administering a therapeutically effective amount of an agent that decreases the level of demyelination in the subject relative to the level of demyelination before administering the agent, wherein the agent comprises nalfurafine.

In one aspect the invention provides a method of accelerating remission from MS in a subject in need thereof, the method comprising administering a therapeutically effective amount of an agent that increases the level of remyelination in the subject relative to the level of remyelination before administering the agent, wherein the agent comprises nalfurafine.

The invention also provides a use of nalfurafine in the manufacture of a medicament for accelerating remission from MS in a subject in need thereof.

The invention also provides nalfurafine for use for accelerating remission from MS in a subject in need thereof.

In another aspect the invention provides a method of treating a demyelinating disease in a subject comprising identifying a subject who would benefit from a decreased level of demyelination and administering to the subject a therapeutically effective amount of an agent that decreases the level of demyelination relative to the level of demyelination before administering the agent, wherein the agent comprises nalfurafine.

In another aspect the invention provides a method of increasing remyelination in a subject comprising identifying a subject who would benefit from an increased level of remyelination and administering to the subject a therapeutically effective amount of an agent that increases the level of remyelination relative to the level of remyelination before administering the agent, wherein the agent comprises nalfurafine.

In the above methods of the invention:

In one embodiment the therapeutically effective amount for a subject is equivalent to a dose of about 0.003 to about 0.3 mg/kg/day in mice.

In one embodiment the subject is human. In one embodiment the method comprises administering about 0.01 to about 5 µg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily.

In some embodiments the method comprises administering less than about 1 µg nalfurafine, preferably less than 1 µg nalfurafine daily.

In some embodiments the method comprises a long duration therapy.

In some embodiments the long duration therapy comprises administration of a therapeutically effective dose of nalfurafine to a subject in need thereof for at least 5 days, at least 6 days, or at least 7 days.

In some embodiments a long duration therapy comprises administration of a therapeutically effective dose of nalfurafine to a subject in need thereof for at least a week, at least 2 weeks, at least 3 weeks, at least 4 weeks, at least 6 weeks, or at least 8 weeks.

In some embodiments the long duration therapy comprises administration for at least 5 days, at least 6 days, at least 7 days, at least 14 days, at least 21 days, at least 28 days, at least 35 days, at least 42 days, at least 45 days, at least 60 days, at least 120 days, at least 240 days, or at least 360 days.

In some embodiments the long duration therapy comprises a dosing gap of at least 1 day.

Other aspects of the invention may become apparent from the following description which is given by way of example only and with reference to the accompanying figures.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art. However, these external documents and references are all cited herein by reference in their entireties or at least to the extent described herein.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

5. BRIEF DESCRIPTION OF THE DRAWINGS

The invention will now be described by way of example only and with reference to the drawings in which:

FIG. 1 is a graph showing the progression of disease in mice which have experimental autoimmune encephalomyelitis (EAE) over 45 days, wherein the mice in Example 1 were treated with 0.01, 0.03, 0.1 or 0.3 mg/kg nalfurafine daily from onset (day 17).

FIGS. 2A-B are two graphs showing the total disability of EAE mice over (A) 45 days and (B) 18 days wherein the mice in Example 2 were treated with 0.03, 0.1 or 0.3 mg/kg nalfurafine daily from onset (day 17).

FIG. 3 is a graph showing the % weight change of EAE mice in Example 3 over 45 days wherein the mice were treated with 0.03, 0.1 or 0.3 mg/kg nalfurafine daily from onset (day 17).

FIGS. 4A-C are three graphs showing immune cell infiltration into the brain of EAE mice in Example 4 after 45 days, wherein the mice were treated with 0.03, 0.1 or 0.3 mg/kg nalfurafine daily from onset (day 17).

FIG. 5 is a graph showing the progression of disease in EAE mice in Example 5 over 45 days, wherein the mice, which had not yet developed EAE, were treated with 0.03, 0.1 or 0.3 mg/kg nalfurafine daily from onset (day 17).

FIGS. 6A-C are a series of Transmission Electron Microscope (TEM) images of spinal cord sections from EAE mice in Example 6 after 45 days, wherein the mice were treated with 0.03 mg/kg nalfurafine daily from onset (day 17).

FIG. 7 is a graph showing weight gain over 65 days of mice in Example 7 treated with 0.3% cuprizone for 5 weeks, wherein the mice were treated with 0.1 mg/kg nalfurafine daily from week 4.

FIG. 8 is a graph showing the rotarod performance score of mice in Example 8 at 9 weeks treated with cuprizone for 5 weeks, wherein the mice were treated with 0.1 mg/kg nalfurafine daily from week 4.

FIGS. 9A-D are a series of TEM imagines of the corpus callosum of mice in Example 9 at 9 weeks treated with cuprizone for 5 weeks, wherein the mice were treated with 0.1 mg/kg nalfurafine daily from week 4.

Figure 19A:
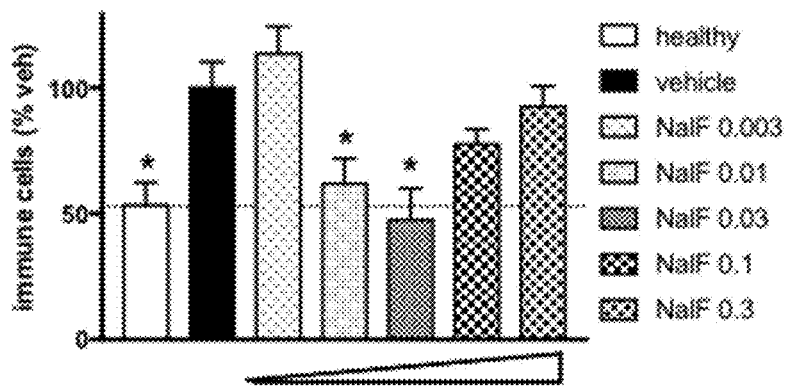
Figure 19B:
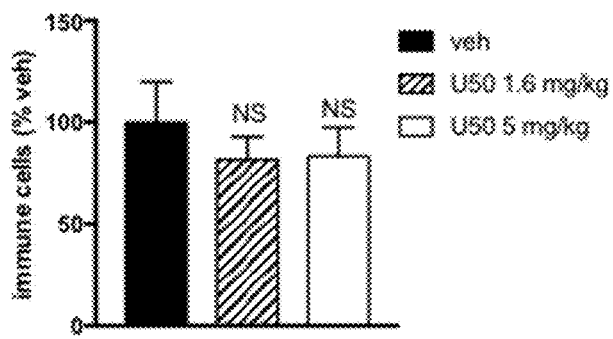

FIGS. 19A-B show that nalfurafine reduces the immune cell infiltration into the brain when administered therapeutically in the EAE model of MS (A) whereas U 50488 does not (B).

Figure 20:
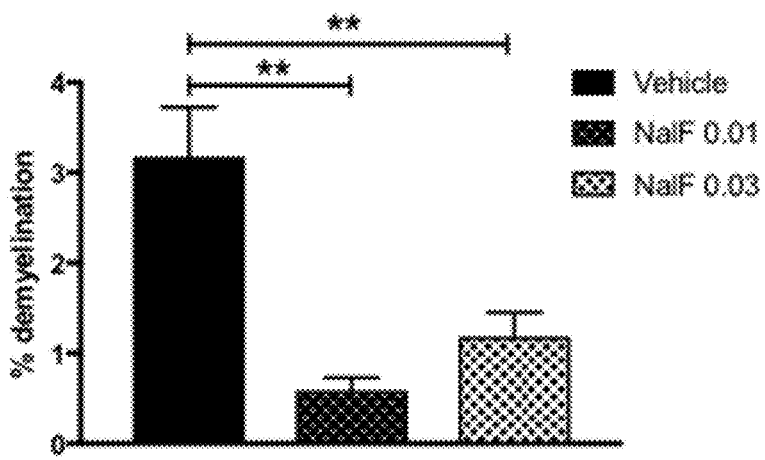

FIG. 20 shows that myelination is improved in mice treated with nalfurafine after the onset of paralysis in the EAE model of MS.

FIGS. 21A-C show that nalfurafine does not alter the proportion of major lymphocyte populations in the spleen during the chronic phase of EAE.

FIGS. 22A-D show that nalfurafine does not alter the overall number of CD4 T helper cells in the spleen but shifts the CD4 T cells from an effector to memory phenotype being suggestive of immune resolution during the chronic phase of EAE.

Figure 23:
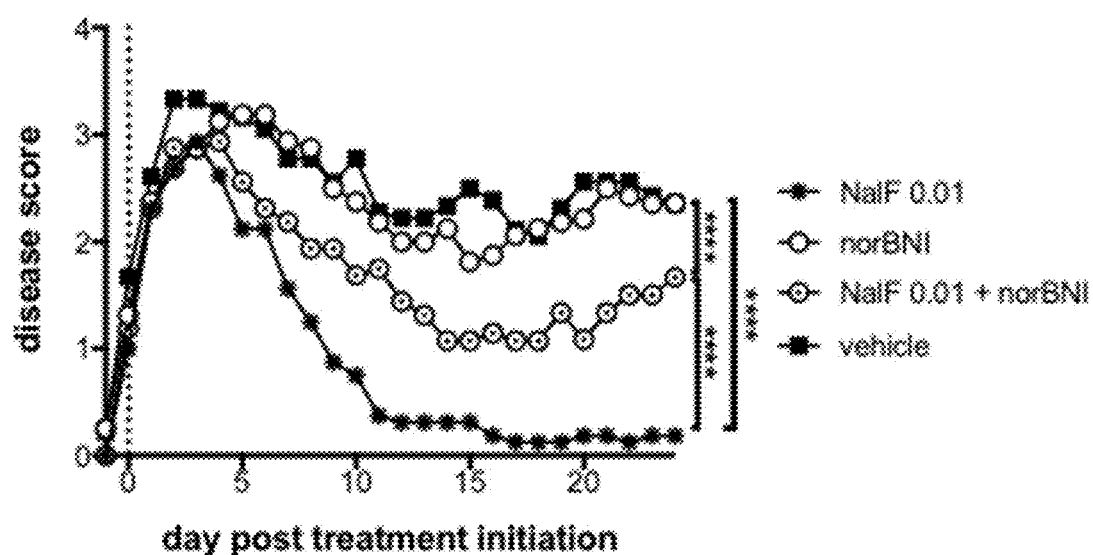

FIG. 23 shows that nalfurafine reduces disease but does not enable full recovery when the kappa opioid receptor (KOR) is blocked.

Figure 24A:
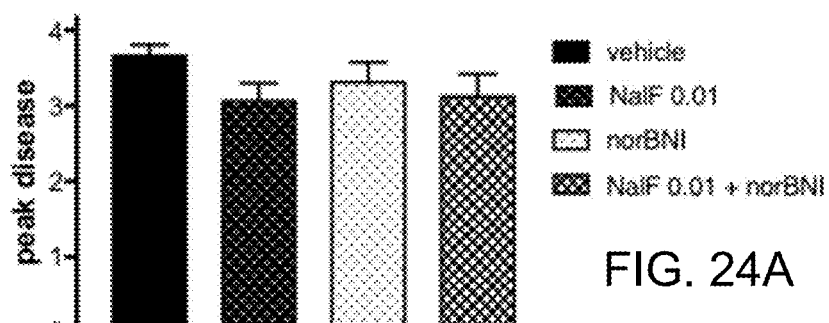
Figure 24B:
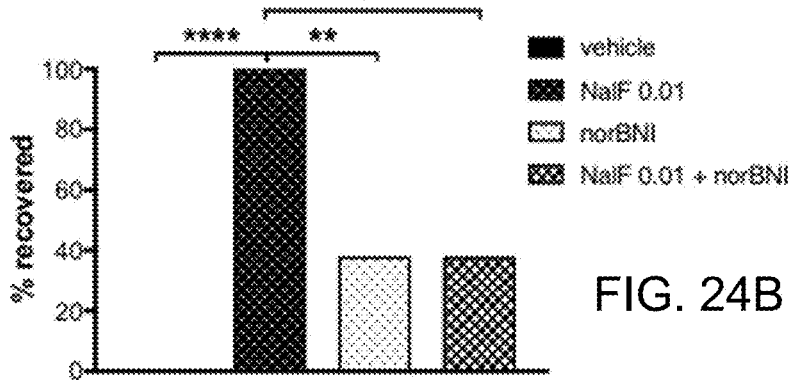
Figure 24C:
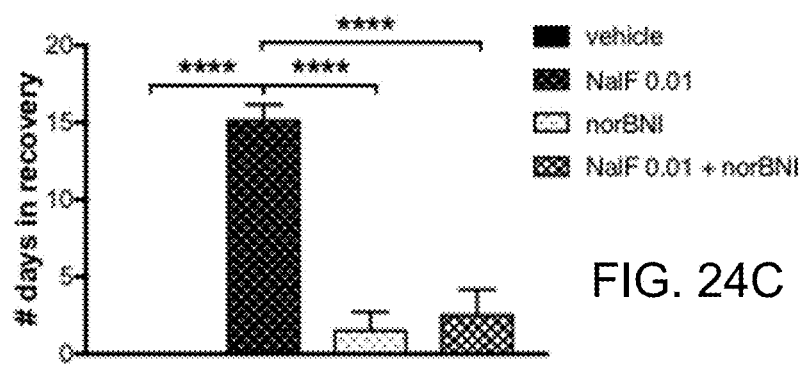
Figure 25A:
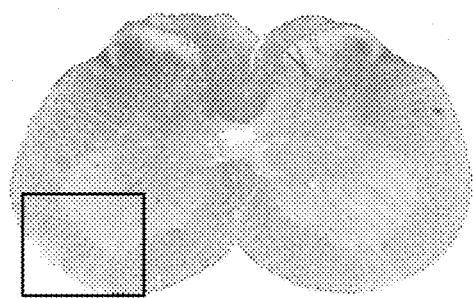
Figure 25B:
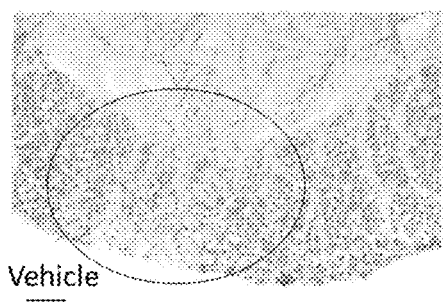
Figure 25C:
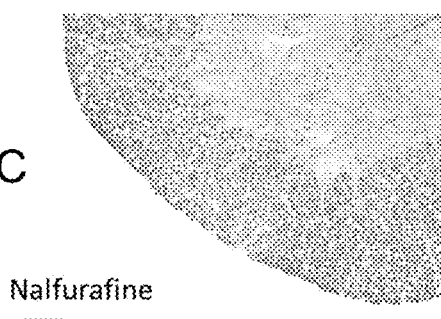
Figure 25D:
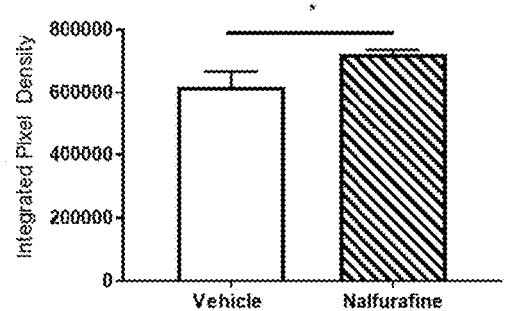

FIGS. 24A-C show that activation of the KOR is required for full recovery from paralysis mediated by nalfurafine.

FIGS. 25A-D show that myelination is improved in mice treated with nalfurafine after the onset of paralysis in the EAE model of MS.

Figure 26A:
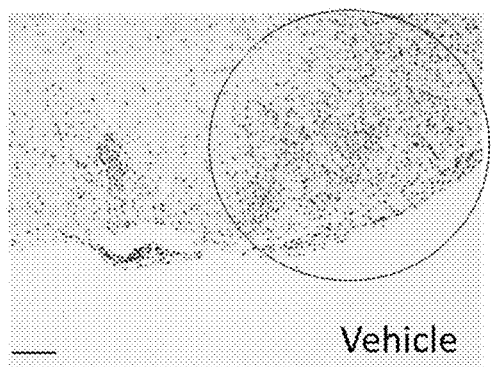
Figure 26B:
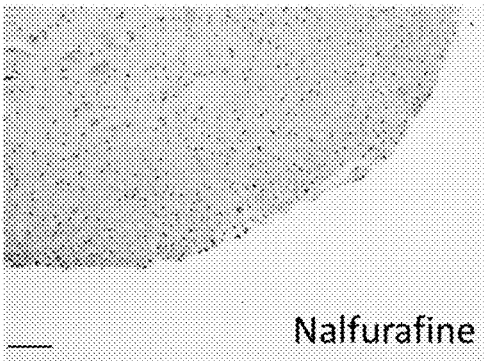
Figure 26C:
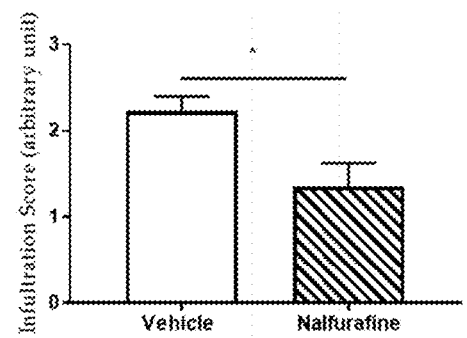

FIGS. 26A-C show that nalfurafine treatment decreases cellular infiltration into the spinal cord when administered therapeutically in the EAE model of MS.

FIGS. 27A-1, 27A-2, and 27B show that nalfurafine treatment reduces the level of activated astrocytes in the spinal cord when administered therapeutically in the EAE model of MS.

Figure 28A:
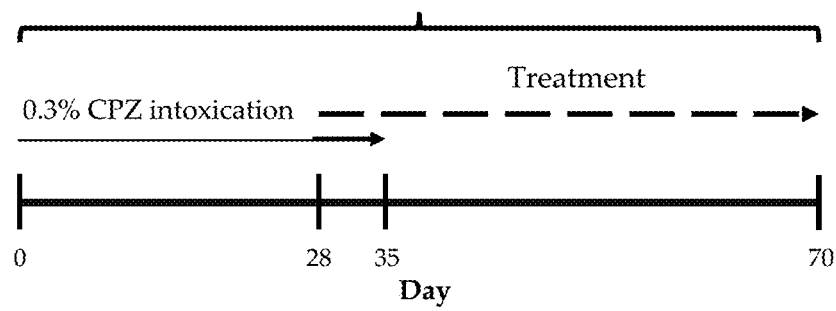
Figure 28B:
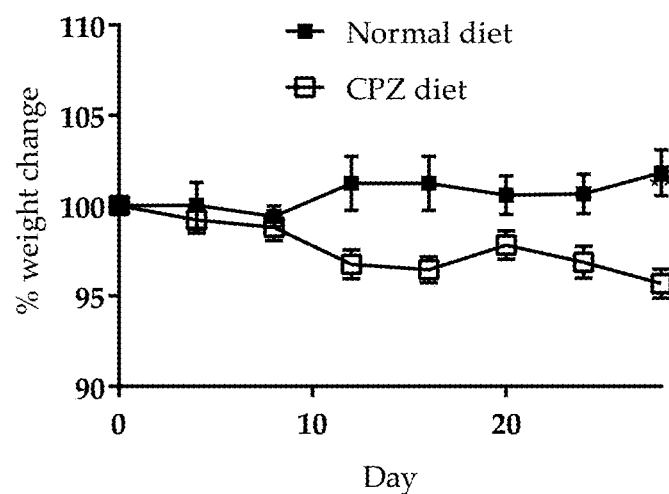
Figure 28C:
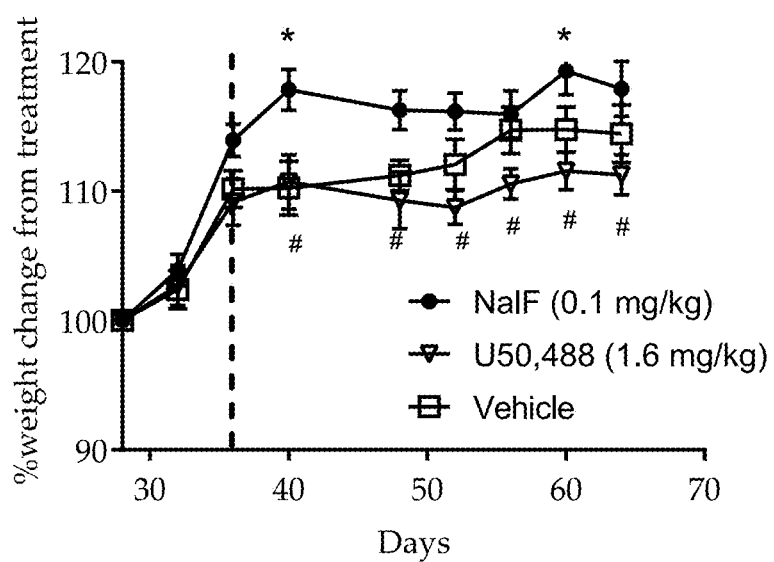

FIGS. 28A-C show that nalfurafine treatment enhances recovery from weight loss when administered therapeutically in the cuprizone model of MS.

FIGS. 29A-G show that nalfurafine treatment enhances remyelination in the brain when administered after demyelination in the cuprizone demyelination disease model of MS.

FIGS. 30A-B show that nalfurafine is more effective at promoting functional recovery than clemastine fumarate, a known remyelinating drug.

FIGS. 31A-1, 31A-2, 31B-1, and 31B-2 show that nalfurafine promotes a greater and more sustained recovery than clemastine fumarate, a known remyelinating drug.

FIGS. 32A-1, 32A-2, and 32B show that nalfurafine promotes recovery in pain threshold when administered after demyelination in the cuprizone demyelination disease model of MS.

6. DETAILED DESCRIPTION

6.1 Nalfurafine

Nalfurafine is a drug commonly prescribed for treatment of uremic pruritus in people with chronic kidney disease. It is a non-narcotic opioid with selective κ-opioid receptor (KOR) agonist activity. The inventors have now found that nalfurafine is a surprisingly effective treatment for demyelinating diseases.

The generic name "nalfurafine" refers to the compound:

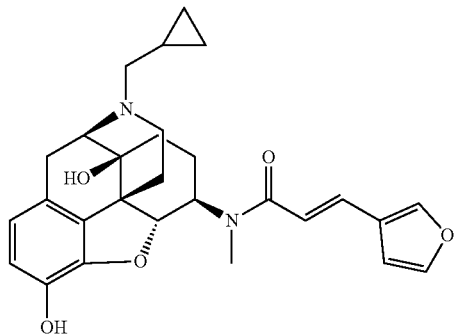 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5]

The IUPAC name for nalfurafine is (E)-N-[(4R,4aS,7R,7aR,12bS)-3-(cyclopropylmethyl)-4a,9-dihydroxy-1,2,4,5,6,7,7a,13-octahydro-4,12-methanobenzofuro[3,2-e]isoquinoline-7-yl]-3-(furan-3-yl)-N-methylprop-2-enamide. Its CAS number is 152657-84-6. Nalfurafine HCl may also be referred to as 17-cyclopropylmethyl-3,14-beta-dihydroxy-4,5-alpha-epoxy-6beta-(N-methyl-trans-3-(3-furyl)acrylamido)morphinan hydrochloride, TRK 820, AC-820 and MT-9938.

As used herein the term "nalfurafine" refers to the compound identified above as well as to its pharmaceutically acceptable salts and solvates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When nalfurafine is basic, salts can be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, ethanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The term "solvate" refers to an aggregate that consists of a solute ion or molecule with one or more solvent molecules. "Solvates" include hydrates, that is, aggregates of a compound of interest with water.

Nalfurafine can be purchased from small molecule suppliers such as Med Chem Express, Monmouth Junction and New Jersey, USA; AdooQ BioScience, Irvine California, USA.

6.2 Pharmaceutical compositions of nalfurafine

There is a lack of effective treatments for demyelinating diseases, including MS, and in particular, there are few effective agents that act to reduce demyelination and/or to increase remyelination. Surprisingly, the inventors have found that pharmaceutical compositions containing nalfurafine can be used to treat demyelination diseases including but not limited to MS by acting to increase remyelination and/or to decrease demyelination.

Accordingly, in one aspect the invention provides a pharmaceutical composition comprising nalfurafine and pharmaceutically acceptable excipients for treating a demyelinating disease in a subject in need thereof.

In another aspect the invention provides a pharmaceutical composition comprising nalfurafine and at least one pharmaceutically acceptable excipient for use for treating a demyelinating disease in a subject in need thereof.

This term "pharmaceutical composition" as used herein encompasses a product comprising one or more active agents, and pharmaceutically acceptable excipients comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by bringing the active agent into association with a liquid carrier, a finely divided solid carrier or both, and then, if necessary, shaping the product into the desired formulation. Said compositions are prepared according to conventional mixing, granulating, or coating methods, respectively, and contain a percentage (%) of the active ingredient and can be determined by a skilled worker in view of the art.

The term "comprising" as used herein means "consisting at least in part of". When interpreting each statement in this specification that includes the term "comprising", features other than that or those prefaced by the term may also be present. Related terms such as "comprise" and "comprises" are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

By "pharmaceutically acceptable excipient" or "pharmaceutically acceptable carrier" it is meant that the excipient or carrier must be compatible with the other ingredients of the formulation and not harmful to the subject to whom the composition is administered.

Pharmaceutical compositions as described herein can be administered topically, orally or parenterally.

For example, the pharmaceutical compositions can be administered orally, including sublingually, in the form of capsules, tablets, elixirs, solutions, suspensions, or boluses formulated to dissolve in, for example, the colon or duodenum. The formulations can comprise excipients such as starch or lactose or flavouring, preserving or colouring agents.

The pharmaceutical compositions can be injected parenterally, for example, intravenously, intramuscularly or subcutaneously. For parenteral administration, the compositions can be formulated in a sterile aqueous solution or suspension that optionally comprises other substances, such as salt or glucose.

The compositions can be administered topically, in the form of sterile creams, gels, pour-on or spot-on formulations, suspensions, lotions, ointments, dusting powders, drug-incorporated dressings, shampoos, collars or transdermal patches. For example, the compositions as described herein can be incorporated into a cream comprising an aqueous or oily emulsion of polyethylene glycols or liquid paraffin; an ointment comprising a white wax soft paraffin base; a hydrogel with cellulose or polyacrylate derivatives or other suitable viscosity modifiers; a dry powder; aerosol with butane, propane, HFA, or CFC propellants; a dressing, such as, a tulle dressing, with white soft paraffin or polyethylene glycol impregnated gauze dressings or with hydrogel, hydrocolloid, or alginate film dressings. The compositions can also be administered intra-ocularly as an eye drop with appropriate buffers, viscosity modifiers (for example, cellulose derivatives), and preservatives (for example, benzalkonium chloride).

The pharmaceutical compositions as described herein can also be incorporated into a transdermal patch comprising nalfurafine. Details of such patches can be found in, for example, WO2015/025766, WO2015/025767, WO2016/208729, WO2017/094337 and WO2017/170933, the details of which are incorporated by reference herein.

For oral administration, capsules, boluses, or tablets can be prepared by mixing the pharmaceutical compositions as described herein with a suitable finely divided diluent or carrier, additionally containing a disintegrating agent and/or binder such as starch, lactose, talc, or magnesium stearate.

For parenteral administration injectable formulations can be prepared in the form of a sterile solution or emulsion.

The compositions described herein can be presented in unit dosage form and can be prepared by any of the methods well known in the art of pharmacy. The term "unit dosage form" means a single dose wherein all active and inactive ingredients are combined in a suitable system, such that the patient or person administering the drug can open a single container or package with the entire dose contained therein and does not have to mix any components together from two or more containers or packages. Typical examples of unit dosage forms are tablets or capsules for oral administration or transdermal patches comprising the unit dosage. These examples of unit dosage forms are not intended to be limiting in any way, but merely to represent typical examples in the pharmacy arts of unit dosage forms.

In another aspect the invention provides unit dosage forms comprising about 0.01 to about 5 mg of nalfurafine and at least one pharmaceutically acceptable carrier or excipient. In one embodiment, the unit dosage form comprises 0.05 to about 2.0 mg of nalfurafine and at least one pharmaceutically acceptable carrier or excipient. In one embodiment the unit dosage form comprises about 0.15 to about 0.6 mg nalfurafine and at least one pharmaceutically acceptable carrier or excipient.

In one aspect the invention provides a unit dosage form comprising about 0.1 to about 10 µg of nalfurafine and at least one pharmaceutically acceptable carrier or excipient. In one embodiment the unit dosage form comprises about 0.5 to about 7.5 µg nalfurafine, about 0.75 to about 5 µg nalfurafine, about 1 to 4 µg nalfurafine, about 2-3 µg nalfurafine, about 2 µg nalfurafine, about 3 µg nalfurafine, about 4 µg nalfurafine or about 5 µg nalfurafine.

In one embodiment the unit dosage form comprises less than about 2 µg, 1.5 µg, 1.0 µg, 0.5 µg, 0.25 µg or 0.1 µg, preferably less than 2 µg, 1.5 µg, 1.0 µg, 0.5 µg, 0.25 µg or 0.1 µg.

In another embodiment, the unit dosage form is for treating a demyelinating disease in a subject in need thereof, preferably wherein the subject has MS. In another embodiment, the unit dosage is formulated for treating a demyelinating disease in a subject in need thereof. In one embodiment the demyelinating disease is MS.

In another embodiment the unit dose is formulated for increasing remyelination in a subject in need thereof, preferably wherein the subject has MS.

In one embodiment, the unit dosage form is for oral administration, preferably the unit dosage form is formulated for oral administration. In another embodiment, the unit dosage form is a transdermal patch.

The term "about" as used herein means a reasonable amount of deviation of the modified term such that the end result is not significantly changed. For example, when applied to a value, the term should be construed as including a deviation of +/−5% of the value.

Pharmaceutical compositions of nalfurafine can be used in combination with other therapies for treating demyelination diseases.

6.3 Therapeutic Uses of Nalfurafine

The inventors have surprisingly found that nalfurafine gives rise to many positive effects in demyelination in MS mouse models. For example, the inventors have found that nalfurafine is effective at treating demyelination in mouse models of EAE and cuprizone-induced demyelination, results that are translatable to treating demyelinating diseases such as MS in humans. The inventors have also found that nalfurafine is unexpectedly effective at increasing remyelination in subjects in need thereof. Accordingly, this drug, which has a proven safety record, could be highly beneficial in the treatment of demyelination diseases and/or for increasing remyelination.

As set out in Examples 1, 10 and 12-18, nalfurafine promotes functional (including full and sustained) recovery from EAE-induced paralysis in male and female mice. Nalfurafine also reduces EAE-induced total disability (see Example 2) and promotes recovery from EAE-induced weight loss (see Example 3). Importantly, the disease score is reduced completely in the examples described herein to <0.5, which is considered to represent a "full recovery" from paralysis in the art, with one exception. A short 4-day time course starting at disease outset was not effective at promoting recovery (Example 11), demonstrating the efficacy of a long duration therapy as described herein.

Nalfurafine reduces immune cell infiltration into the brain in the EAE model of MS (see Example 4) and is more effective than the comparator U-50488, which does not (Example 19. When administered before onset, nalfurafine promotes functional recovery from paralysis, in the EAE model of MS (see Example 5). Myelination is also improved in mice treated with nalfurafine after the onset of paralysis in the EAE model of MS (Examples 6, 20 and 25).

By the examples described herein the inventors show clearly that nalfurafine induces and/or increases remyelination in the EAE model. In Example 6, TEM images of the spinal cords of EAE mice treated with nalfurafine resemble those of the healthy control.

The EAE results were confirmed by cuprizone studies described in Examples 7-9 and 11. In Examples 7 and 28, nalfurafine improved weight gain when administered after cuprizone-induced demyelination. In Example 8, nalfurafine enhanced the functional recovery of coordination and balance in demyelinated mice. Remyelination of the corpus callosum occurred when cuprizone-treated mice were administered nalfurafine (see Examples 9 and 29).

In Example 15 the demonstration of sustained recovery is noteworthy and shows the quite unexpected ability of nalfurafine to reverse, in a sustained manner, the symptoms of demyelination. This surprising result indicates that nalfurafine can mediate sustained recovery of demyelinating diseases including MS.

In Example 21, nalfurafine does not deplete the major immune cell populations in the periphery despite reducing immune cell infiltration into the brain. In example 22, nalfurafine promotes a switch in T helper cells from effector to memory cells suggestive of immune response resolution.

In Examples 23 and 24, the KOR is required for the full effect of nalfurafine but nalfurafine is effective at reducing disease independently of the KOR suggesting the full mechanism by which nalfurafine exerts its effects is more complex than KOR activation.

The positive effects of nalfurafine on mice were particularly surprising at dosages of 0.003 mg/kg to 0.3 mg/kg, which can be converted to an equivalent human dose using the Regan-Shaw equation (Reagan-Shaw S; Nihal M; Ahmad N: *Dose translation from animal to human studies revisited*, FASEB 3. 2007, Oct 17).

Alternatively, dosages of 0.003 to 0.3 mg/kg can be converted to an equivalent human dose using the method of interspecies comparison described herein.

The skilled worker in the art appreciates that there are alternative algorithms that can be used to convert an observed therapeutic dosage from a mouse model into an equivalent human dose once the effective mouse dosage has been demonstrated. Such algorithms can be used effectively by the skilled person to determine the appropriate human dose For example, using a method of interspecies comparison, a skilled worker employs the ratio of the efficacy dose for itch vs the efficacy dose for MS in the same species. This ratio can be applied to the human dose to convert dosage for itch to the dosage for MS. In this case, there is dose data for treating itch in both mouse and human models, and this enables the calculations described below.

61/968,897 Data describing the drug dose that produces 50% of the maximal effect ($ED_{50}$).

| Mouse Model | Route of Administration | ED$_{50}$ (μg/kg) | Complete Inhibition (μg/kg) | Reference |
| --- | --- | --- | --- | --- |
| Substance P induced scratch | IV | 3.77 | 7.5-10 | Winfuran - Assessment report European Medicines Agency, Committee for Medicinal Products for Human Use (EMA/CHMP/138212/2014) |
| Substance P induced scratch | SC | 1.65 | 10 | |
| Substance P induced scratch | PO | 9.61 | 100 (66%) | |
| Morphine induced scratch | SC | 2.34 | 5-10 | |
| Histamine induced scratch | PO | 7.3 | 30-100 | Togashi et al. (2002). Antipruritic activity of the K-opioid receptor agonist, TRK-820. Eur J Pharmacol 435:259 |
| Substance P induced scratch | PO | 19.6 | 100 | |

For itch model the average in vivo efficacy ED$_{50}$ is ~2.71 μg/kg (rounded up to 3 μg/kg) by SC or IV administration (only the data in the top two rows of the table above were used in this calculation). The rationale for this is:

Administration in our EAE study was intraperitoneal (i.p.)

Bioavailability of nalfurafine (as described in Winfuran—Assessment report European Medicines Agency, Committee for Medicinal Products for Human Use (EMA/CHMP/138212/2014):

oral (PO) administration is ~32%
subcutaneous (s.c.) is 96%
intravenous (IV) is 100%

Therefore, s.c. and IV administration will have a similar bioavailability to i.p., whereas PO administration will not due to first-pass effect of hepatic metabolism, and therefore it has been excluded from the calculations. Additionally, the morphine induced scratch model works through a mechanism of action unrelated to that of substance P itch, and therefore was excluded.

Converting Dosage for Itch vs EAE

The calculation assumes that itch response is a biomarker (surrogate) for EAE.

1. Mouse dose for itch is 3 μg/kg/day
2. Mouse dose for EAE is 3 μg/kg/day (effective dose shown in FIG. 10)
3. Therefore, the ratio of itch to EAE in mouse=1
4. Using the ratio of efficacy for itch vs EAE in the same species (mouse) of 1
5. The effective dose in humans for itch of 2.5 μg/body/day
6. Calculation to convert EAE mouse to Human dose prediction:

*EAE mouse dose/(3 μg/kg/day mouse itch×2.5 μg/body/day human itch)=Human MS dose.*

Figure 1:
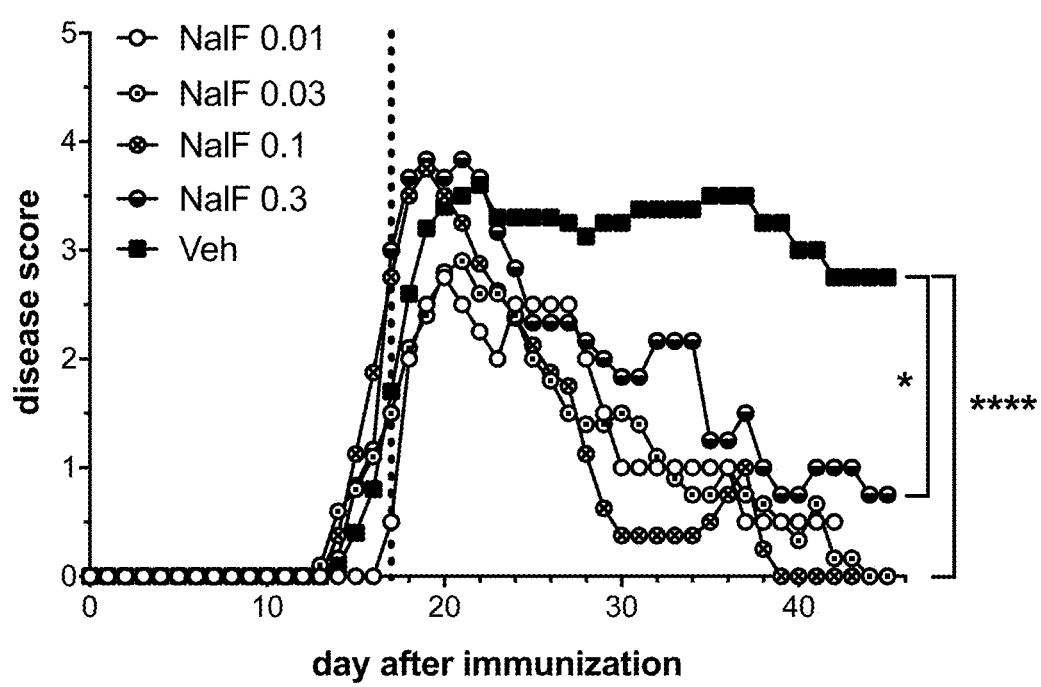

7. Conversion of EAE mouse dose to predicted human MS dose:
   1. 3 μg/kg/day mouse=2.5 μg/body/day for human (FIG. 10)
   2. 10 μg/kg/day mouse=8.33 μg/body/day for human (FIG. 1)
   3. 30 μg/kg/day mouse=25 μg/body/day for human (FIG. 1)
   4. 100 μg/kg/day mouse=83.33 μg/body/day for human (FIG. 1)
   5. 300 μg/kg/day mouse=250 μg/body/day for human (FIG. 1)

As many demyelinating diseases cause horribly debilitating symptoms, any improvement in treatment outcomes provides an important development. The inventors have discovered that nalfurafine is an effective treatment for demyelinating diseases, and in particular MS. In one example, the inventors believe that treatment with nalfurafine will be effective for alleviating the debilitating symptoms related to Clinically Isolated Syndrome (CIS). One of the MS disease courses, CIS generally refers to a first episode of neurologic symptoms associated with MS. Typically, this initial episode is caused by inflammation or demyelination in the central nervous system (CNS), and will last 24 hours or more.

Therefore, in one aspect, the invention provides a method of treating a demyelinating disease in a subject in need thereof, comprising administering a therapeutically effective amount of nalfurafine to the subject.

In another aspect the invention provides a method of treating a demyelinating disease in a subject comprising identifying a subject who would benefit from a decreased level of demyelination and administering to the subject a therapeutically effective amount of an agent that decreases the level of demyelination in the subject relative to the level of demyelination before administering the agent, wherein the agent comprises nalfurafine.

In another aspect the invention provides a method of treating a demyelinating disease in a subject in need thereof, comprising administering to the subject a therapeutically effective amount of an agent that decreases the level of demyelination in the subject relative to the level of demyelination before administering the agent, wherein the agent comprises nalfurafine.

The term "treating" as used herein with reference to a disease or condition refers to the following: (a) ameliorating the disease or condition such as by eliminating or causing regression of or decreasing the severity of the disease or medical condition of the subject being treated relative to an untreated subject according to art-accepted criteria for monitoring the disease or condition (Wattjes et al. (2015). Evidence-based guidelines: MAGNIMS consensus guidelines on the use of MRI in multiple sclerosis—establishing disease prognosis and monitoring patients. Nat. Rev. Neurol. 11, 597-606; Traboulsee et al. (2016). Revised Recommendations of the Consortium of MS Centers Task Force for a Standardized MRI Protocol and Clinical Guidelines for the Diagnosis and Follow-Up of Multiple Sclerosis. AJNR Am. 3. Neuroradiol. 37, 394-401; Toosy et al. (2014). Optic neuritis. Lancet Neurol. 13, 83-99; Ontaneda et al. (2017). Clinical outcome measures for progressive MS trials. Mult. Scler. 23, 1627-1635; Naismith et al. (2012). Diffusion tensor imaging in acute optic neuropathies: predictor of clinical outcomes. Arch. Neurol. 69, 65-71); (b) suppressing the disease or condition such as by slowing or arresting the development of the disease or condition relative to an untreated subject according to art-accepted criteria for monitoring the disease or condition (Oh et al. (2019). Imaging outcome measures of neuroprotection and repair in MS: A consensus statement from NAIMS. Neurology; Sormani et al. (2017). Assessing Repair in Multiple Sclerosis: Outcomes for Phase II Clinical Trials. Neurother. 3. Am. Soc. Exp. Neurother. 14, 924-933; Zhang et al. (2018). Clinical trials in multiple sclerosis: milestones. Ther. Adv. Neurol. Disord. 11; Bjartmar et al. (2003). Axonal loss in the pathology of MS: consequences for understanding the progressive phase of the disease. 3. Neurol. Sci. 206, 165-171; Toosy et al. (2014). Optic neuritis. Lancet Neurol. 13, 83-99) or (c) alleviating a symptom of the disease or condition in the subject relative to an untreated subject according to art-accepted criteria for monitoring the disease or condition (van Munster et al. (2017). Outcome Measures in Clinical Trials for Multiple Sclerosis. CNS Drugs 31, 217-236; Uitdehaag (2018). Disability Outcome Measures in Phase III Clinical Trials in Multiple Sclerosis. CNS Drugs 32, 543-558; Toosy et al. (2014). Optic neuritis. Lancet Neurol. 13, 83-99). In some preferred embodiments "treating" refers to ameliorating as in (a), suppressing as in (b) and/or alleviating as in (c) in a statistically significant manner relative to an appropriate untreated control subject according to art-accepted criteria for monitoring the disease or condition.

In the definition of "treating" the art accepted criteria are one or more of Criteria for measuring disability may include the expanded disability scale, multiple sclerosis functional composite Z-score and multiple sclerosis Impact Scale and Medical Outcomes Study Short Form, imaging of the brain, spinal cord or optic nerve, Multiple Sclerosis Functional Composite, and novel composite measures of disability, in addition to tests evaluating manual dexterity, ambulation, vision (including measures of axial diffusivity, visual acuity, contrast sensitivity, visual evoked potentials (VEPs), and thickness of the retinal nerve fiber layer (RNFL) and cognition.

The subject may show an observable or measurable decrease in one or more of the symptoms associated with or related to the disease or condition as known to those skilled in the art, as indicating improvement. In some embodiments, the disease or condition is a demyelinating disease, preferably MS, and the subject shows an observable and measurable decrease in one or more of the symptoms associated with or related to MS, preferably a decrease in demyelination as known to those skilled in the art, as indicating improvement. In preferred embodiments the improvement is a statistically significant improvement relative to an appropriate untreated control subject according to art-accepted criteria for monitoring the disease or condition.

The terms "decrease" and "reduced" (and grammatical variations thereof) as used herein with reference to demyelination mean any measurable or observable reduction in an amount or level of demyelination or of any symptom of a demyelinating disease that is attributable to demyelination in a treated subject relative to the level of demyelination in an appropriate control (e.g., untreated) subject. In preferred embodiments the measurable or detectable decrease or reduction is a statistically significant decrease or reduction, relative to an appropriate control.

The term "increase" (and grammatical variations thereof as used herein with reference to demyelination means any measurable or observable increase in an amount or level of remyelination or an improvement of any symptom of a demyelinating disease that is attributable to remyelination in a treated subject relative to the level of remyelination in an appropriate control (e.g., untreated) subject; e.g., placebo or non-active agent. An example of quantifying remyelination is demonstrated with treatment with clemastine fumarate using measures of VEPs to evaluate remyelination and recovery. (Green et al. (2017) Clemastine fumarate as a remyelinating therapy for multiple sclerosis (ReBUILD): a randomised, controlled, double-blind, crossover trial. Lancet. 390, 2481-2489; Jankowska-Lech et al. (2019). Peripapillary retinal nerve fiber layer thickness measured by optical coherence tomography in different clinical subtypes of multiple sclerosis. Mult. Scler. Relat. Disord. 27, 260-268; Naismith et al. (2012). Diffusion tensor imaging in acute optic neuropathies: predictor of clinical outcomes. Arch. Neurol. 69, 65-71; Oh et al. (2019). Imaging outcome measures of neuroprotection and repair in MS: A consensus statement from NAIMS. Neurology; Sormani et al. (2017). Assessing Repair in Multiple Sclerosis: Outcomes for Phase II Clinical Trials. Neurother. 3. Am. Soc. Exp. Neurother. 14, 924-933. In preferred embodiments the measurable or detectable reduction is a statistically significant reduction, relative to an appropriate control.

The terms "administration of" or "administering" should be understood to mean providing nalfurafine or a pharmaceutical composition comprising, consisting essentially of, or consisting of, nalfurafine to the subject in need of treatment in a therapeutically useful form for the mode of administration. Nalfurafine can be administered via any suitable route. Potential routes of administration include without limitation oral, parenteral (including intramuscular, subcutaneous, intradermal, intravenous, intraarterial, intramedullary and intrathecal), intraperitoneal, and topical (including dermal/epicutaneous, transdermal, mucosal, transmucosal, intranasal (e.g., by nasal spray or drop), intraocular (e.g., by eye drop), pulmonary (e.g., by inhalation), buccal, sublingual, rectal and vaginal.

The term "therapeutically" as used herein means "at disease onset".

In certain embodiments, nalfurafine is administered via oral dosage forms such as tablets, capsules, syrups, suspensions, and the like. In another embodiment, nalfurafine is administered via a transdermal patch.

The term "therapeutically effective amount" refers to a sufficient quantity of the active agent, in a suitable composition, and in a suitable dosage form to treat the noted disease conditions or to obtain a measurable or observable result such as a decrease in demyelination or an increase in remyelination. The "therapeutically effective amount" will vary depending on the compound, the severity of the demyelination disease, and the species, age, weight, etc., of the subject to be treated.

In one embodiment, the therapeutically effective amount of nalfurafine is the amount equivalent to about 0.003-about 0.3 mg/kg in a mouse which can be converted according to accepted practice into an animal or human subject dosage. For example, using the Reagan-Shaw equation, a therapeutically effective amount of nalfurafine for a dog would be about 0.67-about 2 mg/kg.

In one embodiment, the therapeutically effective amount of nalfurafine is the amount equivalent to about 0.003-about 0.3 mg/kg in a mouse, converted according the method of interspecies comparison described herein. In one embodiment a therapeutically effective amount of nalfurafine for a human is about 0.01 to about 5 µg nalfurafine daily, preferably about 0.01 to about 2.5 µg nalfurafine daily.

In one embodiment the subject is human. In one embodiment the method comprises administering about 0.01 to about 5 µg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily.

In one embodiment the method comprises administering about 0.01 to about 2.5 µg nalfurafine daily, about 0.025 to about 2 µg, about 0.05 to about 1 µg, about 0.075 to about 0.75 µg, about 0.1 to about 0.5 µg, or about 0.225 to about 0.325 µg nalfurafine daily.

In some embodiments the method comprises administering less than about 1 µg nalfurafine daily, preferably less than 1 ug nalfurafine daily.

In one embodiment the method comprises administering about 0.01 to about 0.1 µg nalfurafine daily, about 0.025 to about 0.075 µg, about 0.06 to about 0.04 µg, or about 0.05 µg nalfurafine daily.

In one embodiment the method comprises a long duration therapy.

In some embodiments the long duration therapy comprises administration of a therapeutically effective dose of nalfurafine to a subject in need thereof for at least 5 days, at least 6 days, or at least 7 days.

In some embodiments the long duration therapy comprises administration of a therapeutically effective dose of nalfurafine to a subject in need thereof for at least 5, preferably at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68 69, 70, 71, 72, 73, 74, 75, 76, 77, 78, 79, 80, 81, 82, 83, 84, 85, 86, 87, 88, 89, preferably at least 90 days.

In some embodiments a long duration therapy comprises administration of a therapeutically effective dose of nalfurafine to a subject in need thereof for at least a week, at least 2 weeks, at least 3 weeks, at least 4 weeks, at least 6 weeks, or at least 8 weeks.

In some embodiments the long duration therapy comprises administration for at least 5 days, at least 6 days, at least 7 days, at least 14 days, for at least 21 days, for at least 28 days, for at least 35 days, for at least 42 days, for at least 45 days, for at least 60 days, for at least 120 days, for at least 240 days, or for at least 360 days.

In some embodiments a long duration therapy comprises administration of a therapeutically effective dose of nalfurafine to a subject in need thereof for at least 1 week, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or at least 52 weeks.

In some embodiments a long duration therapy comprises administration of a therapeutically effective dose of nalfurafine to a subject in need thereof for at least 1 month, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or at least 36 months.

In some embodiments the long duration therapy comprises a dosing gap, preferably wherein the dosing gap is at least 1 day.

In some embodiments dosing gap comprises at least 1, 2, 3, 4, 5, 6, 7, 8, 9, 10, 11, 12, 13, or 14 days.

In some embodiments the dosing gap comprises at least 1, 2, 3, 4, 5, 6, 7, 8, 9, 10, 11, or 12 weeks.

In some embodiments the dosing gap comprises at least 1, 2, 3, 4, 5, 6, 7, 8, 9, 10, or 11 months.

The term "demyelinating disease" refers to a disease of the nervous system in which the myelin sheath of neurons is damaged. Demyelinating diseases include demyelinating myelinoclastic diseases and demyelinating leukodystrophic diseases. Treatment of a demyelinating disease can comprise treatment with an agent that decreases demyelination and/or an agent that increases remyelination.

Demyelinating diseases may affect the central nervous system and peripheral nervous system. The central nervous system demyelinating diseases include multiple sclerosis including clinically isolated syndrome (CIS) optic neuritis, Devic's disease, inflammatory demyelinating diseases, central nervous system neuropathies like those produced by Vitamin B12 deficiency, myelopathies like Tabes dorsalis, leukoencephalopathies like progressive multifocal leukoencephalopathy, leukodystrophies, or a combination thereof. The peripheral nervous system demyelinating diseases include Guillain-Barre syndrome and its chronic counterpart, chronic inflammatory demyelinating polyneuropathy, anti-MAG peripheral neuropathy, Charcot Marie Tooth (CMT) disease, copper deficiency, progressive inflammatory neuropathy, or a combination thereof. The term "subject" refers to a mammal, more preferably a human, or companion animal. Preferred companion animals include cats, dogs and horses. Other mammalian subjects include agricultural animals, including horses, pigs, sheep, goats, cows, deer, or fowl: and laboratory animal, including monkeys, rats, mice, rabbits and guinea pig.

The invention also provides a use of nalfurafine in the manufacture of a medicament for treating a demyelinating disease in a subject in need thereof.

The invention also provides a use of nalfurafine in the manufacture of a medicament for increasing remyelination in a subject in need thereof.

The invention also provides nalfurafine for use for treating a demyelinating disease.

The invention also provides nalfurafine for use for increasing remyelination.

In one embodiment the disease is a demyelinating myelinoclastic disease.

In one embodiment the disease is a demyelinating leukodystrophic disease.

In one embodiment the demyelinating disease is a central nervous system demyelinating disease. In one embodiment the central nervous system demyelinating disease is selected from the group comprising MS (including clinically isolated syndrome; CIS), optic neuritis, Devic's disease, inflammatory demyelinating diseases, central nervous system neuropathies, myelopathies like Tabes dorsalis, leukoencephalopathies, leukodystrophies, or a combination thereof.

In one embodiment the demyelinating disease is MS.

In another embodiment the demyelinating disease is a peripheral nervous system demyelinating disease. In one embodiment the peripheral nervous system demyelinating disease is elected from the group comprising Guillain-Barre syndrome and its chronic counterpart, chronic inflammatory demyelinating polyneuropathy, anti-myelin associated glycoprotein (MAG) peripheral neuropathy, Charcot Marie Tooth (CMT) disease, copper deficiency and progressive inflammatory neuropathy.

In another aspect the invention provides a method of increasing remyelination in a subject in need thereof, comprising administering a therapeutically effective amount of nalfurafine to the subject.

In another aspect the invention provides a method of increasing remyelination in a subject comprising identifying a subject who would benefit from an increased level of remyelination and administering to the subject a therapeutically effective amount of an agent that increases the level of remyelination in the subject relative to the level of remyelination before administering the agent, wherein the agent comprises nalfurafine.

In another aspect the invention provides a method of increasing remyelination in a subject in need thereof, comprising administering to the subject a therapeutically effective amount of an agent that increases the level of remyelination in the subject relative to the level of remyelination before administering the agent, wherein the agent comprises nalfurafine.

Specifically contemplated as embodiments of the invention described herein relating to a method of increasing remyelination in a subject are all of the embodiments of the invention set forth herein relating to the aspects of the invention that are methods of decreasing demyelination, methods of treating MS, methods of attenuating demyelination, methods of accelerating remission of MS, and methods of treating a demyelinating disease.

In another aspect the invention provides a method of attenuating demyelination in a subject in need thereof, comprising administering a therapeutically effective amount of nalfurafine to the subject and thereby attenuating a level of demyelination in the subject relative to the level of demyelination when nalfurafine is not administered.

In another aspect the invention provides a method of attenuating demyelination in a subject in need thereof, comprising administering a therapeutically effective amount of an agent that decreases the level of demyelination in the subject relative to the level of demyelination before administering the agent and/or that increases the level of remyelination in the subject relative to the level of remyelination before administering the agent wherein the agent comprises nalfurafine.

In one embodiment the subject is human. In one embodiment the method comprises administering about 0.01 to about 5 µg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily.

In one embodiment the method comprises administering about 0.01 to about 2.5 µg nalfurafine daily, about 0.025 to about 2 µg, about 0.05 to about 1 µg, about 0.075 to about 0.75 µg, about 0.1 to about 0.5 µg, or about 0.225 to about 0.325 µg nalfurafine daily.

In some embodiments the method comprises administering less than about 1 µg nalfurafine daily, preferably less than 1 ug nalfurafine daily.

In one embodiment the method comprises administering about 0.01 to about 0.1 µg nalfurafine daily, about 0.025 to about 0.075 µg, about 0.06 to about 0.04 µg, or about 0.05 µg nalfurafine daily.

The term "attenuation of demyelination" means in certain embodiments that the amount or level of demyelination in the subject as a result of the disease or as a symptom of the disease is reduced when compared to otherwise identical conditions in an appropriate control subject or at an appropriate control reference timepoint and/or in certain embodiments that the amount or level of remyelination in the subject is increased when compared to an otherwise identical conditions in an appropriate control subject or at an appropriate control reference timepoint. In some preferred embodiments the reduction or increase as compared to the appropriate control is a statistically significant reduction or increase.

In certain preferred embodiments, the term "attenuation of demyelination" thus means that the amount of or level demyelination in the subject as a result of the disease or as a symptom of the disease is reduced or decreased in a statistically significant manner when compared to a suitable control as would be understood by a person of skill in the art in view of the present disclosure and/or the amount or level of remyelination in the subject is increased in a statistically significant manner when compared to a suitable control as would be understood by a person of skill in the art in view of the present disclosure.

Similarly, the term "improvement in nerve function" refers to a quantifiable improvement in function having a statistically different change in a measurable parameter relative to an appropriate control as recognized by a person of skill in the art. In some embodiments the improvement in function has a statistically significant change in the measurable parameter. In one embodiment the measurable parameter is the disease score as described in Example 1.

Symptoms attributable to demyelination will vary depending on the disease but may include, for example but not limited to, neurological deficits, such as chronic pain, cognitive impairment (including memory, attention, conceptualization and problem-solving skills) and information processing; paresthesia in one or more extremities, in the trunk, or on one side of the face; weakness or clumsiness of a leg or hand; or visual disturbances, e.g. partial blindness and pain in one eye (retrobulbar optic neuritis), dimness of vision, or scotomas.

The invention also provides a use of nalfurafine in the manufacture of a medicament for attenuating demyelination in a subject in need thereof.

The invention also provides nalfurafine for use for attenuating demyelination in a subject in need thereof.

In another aspect the invention provides a method of treating MS in a subject in need thereof, comprising administering a therapeutically effective amount of nalfurafine to the subject. The subject can suffer from any type of MS including CIS, RRMS, PRMS, SPMS, PRMS or MS that follows a different and/or undefined disease course.

The invention also provides a use of nalfurafine in the manufacture of a medicament for treating MS in a subject in need thereof.

The invention also provides nalfurafine for use for treating MS in a subject in need thereof.

In one embodiment the subject has RRMS. In one embodiment the subject has PPMS. In one embodiment the subject has, or is diagnosed as having, SPMS. In one embodiment the subject has, or is diagnosed as having, PRMS. In one embodiment the subject has, or is diagnosed as having, Clinically Isolated Syndrome (CIS).

In another aspect the invention provides a method of treating MS in a subject in need thereof, comprising administering to the subject a therapeutically effective amount of an agent that decreases a level of demyelination in the subject relative to the level before administering the agent and/or that increases a level of remyelination in the subject in the subject relative to the level before administering the agent, wherein the agent comprises nalfurafine.

In some embodiments the methods of treating MS set forth herein can comprise one or more of the following steps selected from the group consisting of diagnosing MS in the subject, testing for demyelination in the subject, testing for a reduction or reversal in demyelination in the subject, testing for remyelination in the subject, testing for a level of paralysis or a reduction or reversal of a level of paralysis in the subject, and testing for a decrease or increase of coordination and/or balance in the subject.

In one embodiment a method of treating MS and/or of treating a demyelinating disease and/or of attenuating demyelination and/or of increasing remyelination comprises identifying a subject who would benefit from a level of decreased demyelination.

In some embodiments a subject who would benefit from a level of decreased demyelination and/or a level of increased remyelination is identified on the basis of exhibiting one or more clinical symptoms of MS including, but not limited to: loss of sensitivity or changes in sensation such as tingling, pins and needles or numbness, muscle weakness of variable severity, very pronounced reflexes, muscle spasms, or difficulty in moving; difficulties with coordination and balance (ataxia); spasticity; problems with speech or swallowing, visual problems (nystagmus, optic neuritis or double vision), fatigue, acute or chronic pain, facial pain (trigeminal neuralgia), bladder and bowel difficulties, incontinence, reduced cognitive ability, depression, anxiety and other emotional abnormalities, sexual dysfunction, Uhthoff's phenomenon (a worsening of symptoms due to exposure to higher than usual temperatures), and Lhermitte's sign (an electrical sensation that runs down the back when bending the neck).

In some embodiments the therapeutically effective amount of nalfurafine to be administered to a human subject is about 0.01 to about 5 mg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily.

In some embodiments the therapeutically effective amount of nalfurafine to be administered to a human subject is about 0.01 to about 2.5 µg nalfurafine daily, about 0.025 to about 2 µg, about 0.05 to about 1 µg, about 0.075 to about 0.75 µg, about 0.1 to about 0.5 µg, or about 0.225 to about 0.325 µg nalfurafine daily.

In some embodiments the method comprises administering less than about 1 µg nalfurafine daily, preferably less than 1 ug nalfurafine daily.

In some embodiments the therapeutically effective amount of nalfurafine to be administered to a human subject is about 0.01 to about 0.1 µg nalfurafine daily, about 0.025 to about 0.075 µg, about 0.06 to about 0.04 µg, or about 0.05 µg nalfurafine daily.

In one embodiment the treatment results in one or more clinical outcomes as compared to subjects not treated with nalfurafine, selected from the group consisting of:
(a) a decrease in MS disease progression;
(b) a decrease in MS disease severity;
(c) a decrease in nerve cell demyelination;
(d) a decrease in frequency or severity of relapsing MS attacks;
(e) a decrease in MS clinical symptoms;
(f) the healing of damaged nerve tissue (neuro-restoration);
(g) an increase in remyelination of demyelinated nerves in the central nervous system (neuro-restoration/protection);
(h) the protection of damaged nerve tissue from further disease activity (neuro-protection);
(i) the promotion neuronal outgrowth (neuro-regeneration) in the central nervous system;
(j) a decrease in disability caused by MS;
(k) an improvement of nerve function; and
(l) an enhanced rate of remission.

In another embodiment the treatment results in a reduction of one or more clinical symptoms of MS including, but not limited to loss of sensitivity or changes in sensation such as tingling, pins and needles or numbness, muscle weakness of variable severity, very pronounced reflexes, muscle spasms, or difficulty in moving; difficulties with coordination and balance (ataxia); spasticity; problems with speech or swallowing, visual problems (nystagmus, optic neuritis or double vision), fatigue, acute or chronic pain, facial pain (trigeminal neuralgia), bladder and bowel difficulties, incontinence, reduced cognitive ability, depression, anxiety and other emotional abnormalities, sexual dysfunction, Uhthoff's phenomenon (a worsening of symptoms due to exposure to higher than usual temperatures), and Lhermitte's sign (an electrical sensation that runs down the back when bending the neck).

In one aspect the invention provides a method of accelerating remission of MS in a subject in need thereof, the method comprising administering a therapeutically effective amount of nalfurafine to the subject.

In one aspect the invention provides a method of accelerating remission from MS in a subject in need thereof, the method comprising administering a therapeutically effective amount of an agent that decreases the level of demyelination in the subject relative to the level of demyelination before administering the agent, wherein the agent comprises nalfurafine.

In one aspect the invention provides a method of accelerating remission from MS in a subject in need thereof, the method comprising administering a therapeutically effective amount of an agent that increases the level of remyelination in the subject relative to the level of remyelination before administering the agent, wherein the agent comprises nalfurafine.

The invention also provides a use of nalfurafine in the manufacture of a medicament for accelerating remission from MS in a subject in need thereof.

The invention also provides nalfurafine for use in accelerating remission from MS in a subject in need thereof.

In some embodiments the therapeutically effective amount of nalfurafine to be administered to a human subject is about 0.01 to about 5 µg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily.

In some embodiments the therapeutically effective amount of nalfurafine to be administered to a human subject is about 0.01 to about 2.5 µg nalfurafine daily, about 0.025 to about 2 µg, about 0.05 to about 1 µg, about 0.075 to about 0.75 µg, about 0.1 to about 0.5 µg, or about 0.225 to about 0.325 µg nalfurafine daily.

In some embodiments the method comprises administering less than about 1 µg nalfurafine daily, preferably less than 1 ug nalfurafine daily.

In some embodiments the therapeutically effective amount of nalfurafine to be administered to a human subject is about 0.01 to about 0.1 µg nalfurafine daily, about 0.025 to about 0.075 µg, about 0.06 to about 0.04 µg, or about 0.05 µg nalfurafine daily.

The term "enhanced remission of MS" as used herein, means that the start of the remission process is reached faster and/or the rate at which remission is achieved is faster (as compared to subjects not treated with nalfurafine).

Remission of MS can be measured using any technique known in the art including but not limited to physical disability status, biological markers and brain scans using MRI.

In one aspect the invention provides a method of treating MS in a human subject in need thereof, the method comprising administering to the subject about 0.01 to about 5 mg nalfurafine daily, about 0.05 to about 2.0 mg, about 0.15 to 0.6 mg nalfurafine daily, wherein the treatment results in one or more clinical outcomes as compared to subjects not treated with nalfurafine selected from the group consisting of:
(a) a decrease in MS disease progression;
(b) a decrease in MS disease severity;
(c) a decrease in nerve cell demyelination;
(d) a decrease in frequency or severity of relapsing MS attacks;
(e) a decrease in MS clinical symptoms;
(f) the healing of damaged nerve tissue (neuro-restoration);
(g) an increase in remyelination of demyelinated nerves in the central nervous system (neuro-restoration/protection);
(h) the protection of damaged nerve tissue from further disease activity (neuro-protection);
(i) the promotion neuronal outgrowth (neuro-regeneration) in the central nervous system;
(j) a decrease in disability caused by MS;
(k) an improvement of nerve function; and
(l) an enhanced rate of remission.

In one aspect the invention provides a method of treating MS in a human subject in need thereof, the method comprising administering to the subject about 0.01 to about 5 µg nalfurafine daily, about 0.01 to about 4 µg, about 0.01 to about 3 µg, about 0.01 to about 2.5 µg, about 0.01 to about 2 µg, about 0.01 to about 1.5 µg, about 0.01 to about 1 µg, about 0.01 to about 0.75 µg, about 0.01 to about 0.5 µg, or about 0.25 µg nalfurafine daily, wherein the treatment results in one or more clinical outcomes as compared to subjects not treated with nalfurafine selected from the group consisting of:
(a) a decrease in MS disease progression;
(b) a decrease in MS disease severity;
(c) a decrease in nerve cell demyelination;
(d) a decrease in frequency or severity of relapsing MS attacks;
(e) a decrease in MS clinical symptoms;
(f) the healing of damaged nerve tissue (neuro-restoration);
(g) an increase in remyelination of demyelinated nerves in the central nervous system (neuro-restoration/protection);
(h) the protection of damaged nerve tissue from further disease activity (neuro-protection);
(i) the promotion neuronal outgrowth (neuro-regeneration) in the central nervous system;
(j) a decrease in disability caused by MS;
(k) an improvement of nerve function; and
(l) an enhanced rate of remission.

In some embodiments the therapeutically effective amount of nalfurafine to be administered to a human subject is about 0.01 to about 2.5 µg nalfurafine daily, about 0.025 to about 2 µg, about 0.05 to about 1 µg, about 0.075 to about 0.75 µg, about 0.1 to about 0.5 µg, or about 0.225 to about 0.325 µg nalfurafine daily.

In some embodiments the method comprises administering less than about 1 µg nalfurafine daily, preferably less than 1 ug nalfurafine daily.

In some embodiments the therapeutically effective amount of nalfurafine to be administered to a human subject is about 0.01 to about 0.1 µg nalfurafine daily, about 0.025 to about 0.075 µg, about 0.06 to about 0.04 µg, or about 0.05 µg nalfurafine daily.

In another aspect the invention provides a method of treating a demyelinating disease in a subject comprising identifying a subject who would benefit from a decreased level of demyelination and administering to the subject a therapeutically effective amount of an agent that decreases the level of demyelination relative to the level of demyelination before administering the agent, wherein the agent comprises nalfurafine.

In another aspect the invention provides a method of increasing remyelination in a subject comprising identifying a subject who would benefit from an increased level of remyelination and administering to the subject a therapeutically effective amount of an agent that increases the level of remyelination relative to the level of remyelination before administering the agent, wherein the agent comprises nalfurafine.

Specifically contemplated as embodiments of the invention described herein relating to nalfurafine for use in decreasing demyelination, attenuating demyelination, accelerating remission of MS, treating MS, treating a demyelinating disease and increasing remyelination are all of the embodiments of the invention set forth herein relating to the aspects of the invention that are methods of decreasing demyelination, attenuating demyelination, accelerating remission of MS, treating MS, treating a demyelinating disease and increasing remyelination.

Additionally, specifically contemplated as embodiments of the invention described herein relating to the use of nalfurafine in the manufacture of a medicament for decreasing demyelination, attenuating demyelination, accelerating remission of MS, treating MS or for increasing remyelination are all of the embodiments of the invention set forth herein relating to the aspects of the invention that are methods of decreasing demyelination, attenuating demyelination, accelerating remission of MS, treating MS, treating a demyelinating disease and increasing remyelination.

In addition, specifically contemplated herein for all recited method, use and nalfurafine for use aspects of the invention are all of the embodiments set out herein that relate to long duration therapy and dosing gaps in long duration therapy.

The invention consists in the foregoing and also envisages constructions of which the following gives examples only and in no way limit the scope thereof.

6.4 EXAMPLES

Example 1: Nalfurafine Promotes Functional Recovery From Paralysis When Administered Therapeutically in the Experimental Autoimmune Encephalomyelitis (EAE) Model of MS Experimental detail: Female, C57BL/6 mice were immunized subcutaneously (s.c.) in the hind flanks to induce EAE using myelin oligodendrocyte glycoprotein (MOG) peptide 35-55 (50 mg/mouse) in complete Freund's adjuvant containing heat-killed *Mycobacterium tuberculosis* (500 µg/mouse). In addition, pertussis toxin (200 ng/mouse) was administered intraperitoneally (i.p.) on days 0 and 2. Mice were weighed and scored daily. On day 17 (vertical dotted line in FIG. 1), mice were started on daily treatment with vehicle only (Veh; 10% tween and 10% DMSO in saline) or nalfurafine at 0.3, 0.1, 0.03, or 0.01 mg/kg by i.p. injection. Nalfurafine was obtained from the University of Kansas, Synthetic Chemical Biology Core Laboratory (97.6% pure by HPLC). Treatment allocation was blinded. The disease was scored from 0-5 with 0 (normal), 1 (partial tail paralysis), 2 (full tail paralysis), 3 (one hind limb paralysed or severe disability in both hind limbs), 4 (complete paralysis of both hind limbs) and 5 (moribund). This model is a standard disease model for multiple sclerosis and is described in White et al. 2018. *Scientific Reports.* 8:259 which is incorporated herein by reference in its entirety. Shown in FIG. 1 are results combined from 2 independent experiments. ****$p<0.0001$ & *$p<0.05$ by one-way ANOVA with Dunnett's multiple comparison test.

Interpretation and impact: The results demonstrate that nalfurafine is able to treat on-going disease. The reduction of disease in all nalfurafine-treated groups indicates recovery from paralysis, which is complete at some doses (0.1 and 0.03 mg/kg) and unusual in this model. Finally, the dose at which nalfurafine shows the most rapid recovery in this example is 0.1 mg/kg with doses above and below this level appearing less effective.

Figure 2A:
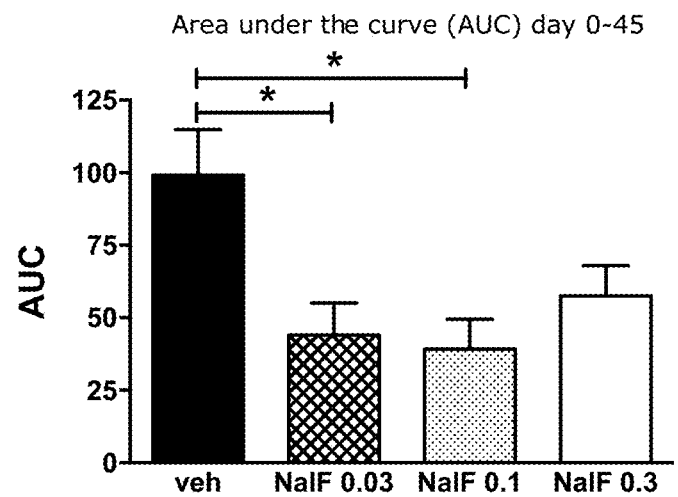
Figure 2B:
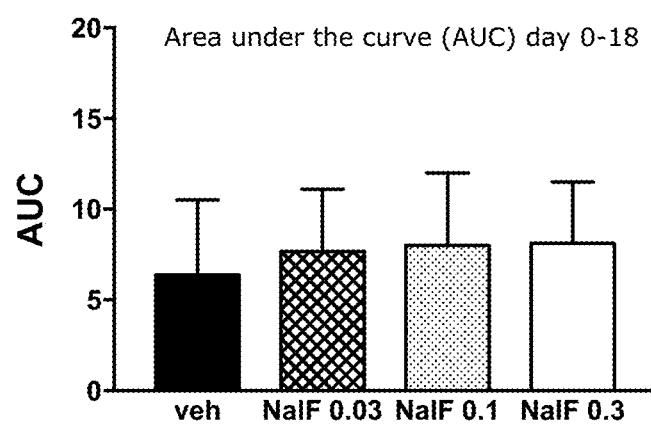

Example 2: Nalfurafine Reduces Total Disability When Administered Therapeutically in the EAE Model of MS Experimental detail: EAE was induced in female C57BL/6 mice as described in Example 1. On day 17, mice were started on daily treatment with vehicle only (Veh) or nalfurafine at 0.3, 0.1, or 0.03 mg/kg by i.p. injection. The area under the curve (AUC) was calculated for each mouse based upon the daily disease score and represents the total disability experienced. Shown in FIGS. 2A-B are results from 1 representative experiment. *$p<0.05$ by one-way ANOVA with Dunnett's multiple comparison test.

Interpretation and impact: Despite all treatment groups having similar disease scores at the start of treatment (lower graph), mice treated daily with nalfurafine had significantly lower total disability by day 45 after immunization to induce EAE (upper graph). Doses of 0.03 and 0.1 mg/kg nalfurafine had the greatest effect at reducing disability. The 0.1 mg/kg nalfurafine dose results in a 60% reduction in disease.

Without wishing to be bound by theory, the inventors believe that the results in Example 2 highlight the benefits of treatment with nalfurafine over a period of at least a week. Accordingly, in some embodiment's administration comprises administration for at least 7 days, at least 14 days, at least 30 days, at least 45 days, at least 60 days, at least 120 days, at least 240 days, or at least 360 days.

Example 3: Nalfurafine Promotes Recovery From EAE-Induced Weight Loss When Administered Therapeutically Experimental detail: EAE was induced in female C57BL/6 mice as described in Example 1. Mice were weighed daily and the % change in body weight calculated. On day 17 (vertical dotted line in FIG. 3), mice were started on daily treatment with vehicle only (Veh) or nalfurafine at 0.3, 0.1, or 0.03 mg/kg by i.p. injection.

Figure 3:
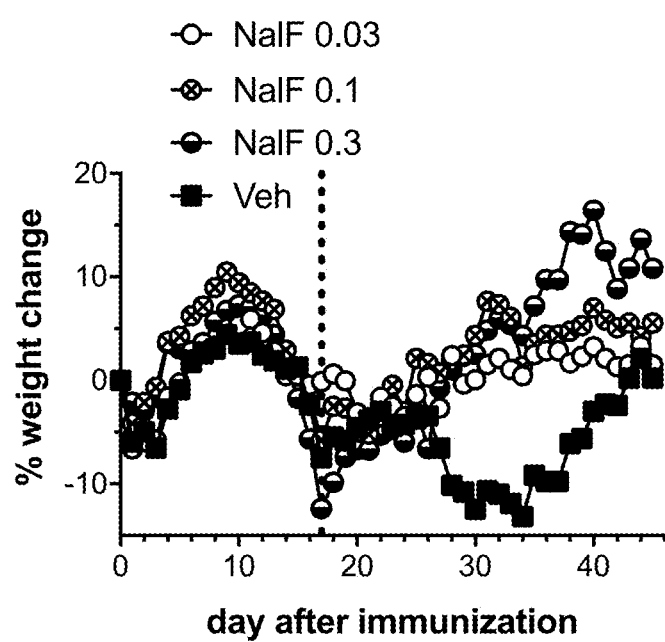

Interpretation and impact: As shown in FIG. 3, at onset of disease, mice rapidly lose weight. Once treatment with nalfurafine is initiated (vertical dotted line), mice recover from EAE-induced weight loss.

Example 4: Nalfurafine Reduces the Immune Cell Infiltration Into the Brain When Administered at Low Doses Therapeutically in the EAE Model of MS Experimental detail: EAE was induced in female C57BL/6 mice as described in Example 1. On day 17, mice were started on daily treatment with vehicle only (Veh) or nalfurafine at 0.3, 0.1, or 0.03 mg/kg by i.p. injection. On day 45 after immunization to induce EAE, mice were culled, and immune cells isolated from the brains. Isolation was by Percoll gradient as described in White et al. 2018. *Scientific Reports.* 8:259. Once isolated, cells were stained with fluorescently labelled antibodies to identify specific immune cell types and analysed by flow cytometry. All infiltrating immune cells were identified by $CD45^{high}$ expression; CD4 T cells were identified as $CD45^{high}CD4+$, and macrophages as $CD45^{high}CD11b^+Gr-1^-$. The relative number of cells is expressed as a ratio to microglia (MG), a brain resident immune cell identified as $CD45^{medium}CD11b^+$. *$p<0.05$ by one-way ANOVA with Dunnett's multiple comparison test.

Figure 4A:
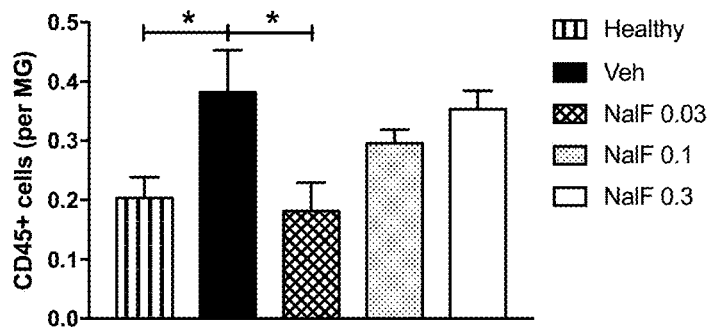
Figure 4B:
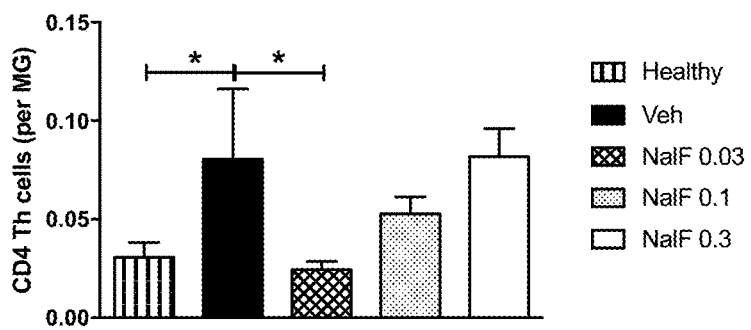
Figure 4C:
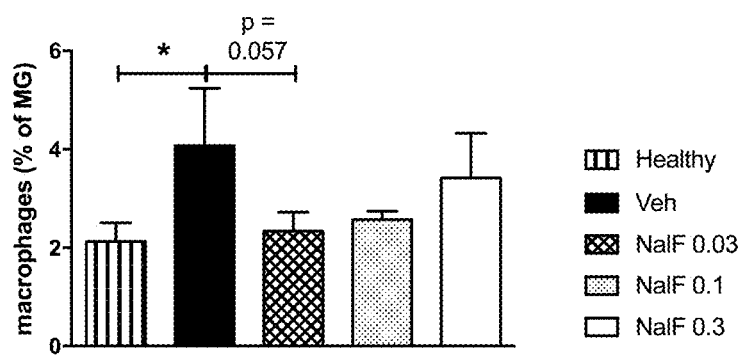

Interpretation and impact: As shown in FIGS. 4A-C, at day 45, there was a significant elevation in immune cells in the brains of vehicle-treated EAE mice compared to healthy animals. Treatment with 0.03 mg/kg nalfurafine significantly reduced the number of infiltrating immune cells suggesting that at this dose, nalfurafine can have immunomodulatory properties. Interestingly, while mice treated with 0.1 nalfurafine had similar levels of infiltrating cells as vehicle-treated animals, these mice had no overt signs of disease and had recovered fully from paralysis (FIG. 1).

Figure 5:
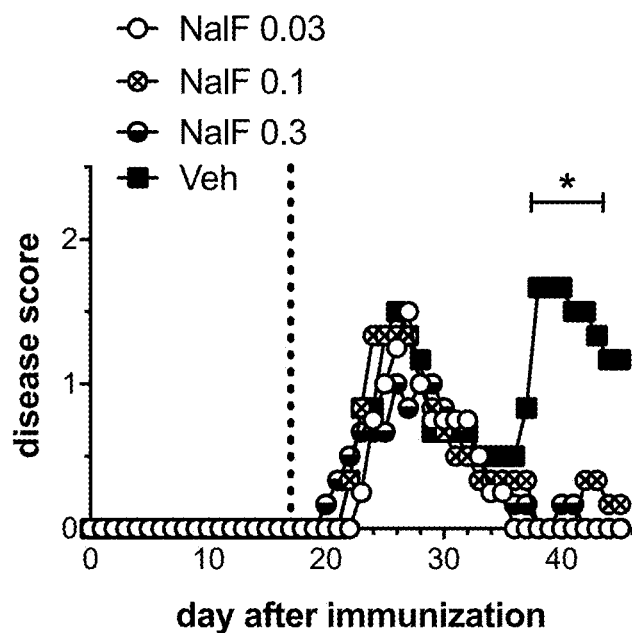

Example 5: Nalfurafine Promotes Functional Recovery From Paralysis When Administered Before the Onset of Paralysis in the EAE Model of MS Experimental detail: EAE was induced in female C57BL/6 mice as described in Example 1. On day 17 (vertical dotted line in FIG. 5), mice were started on daily treatment with vehicle only (Veh) or nalfurafine at 0.3, 0.1, or 0.03 mg/kg by i.p. injection. Shown in FIG. 5 are results in mice that were not sick at the time of treatment but developed disease later. *$p<0.05$ by two-way ANOVA with Holm-Sidak's multiple comparison test.

Interpretation and impact: Treating with nalfurafine prior to disease onset did not alter the onset of disease. However, treatment with nalfurafine led to a rapid recovery from paralysis compared to vehicle-treated mice. These data suggest that treating with nalfurafine will also be effective at reducing total disability if administered before disease but may not prevent onset.

Figures 6A, 6B, 6C:
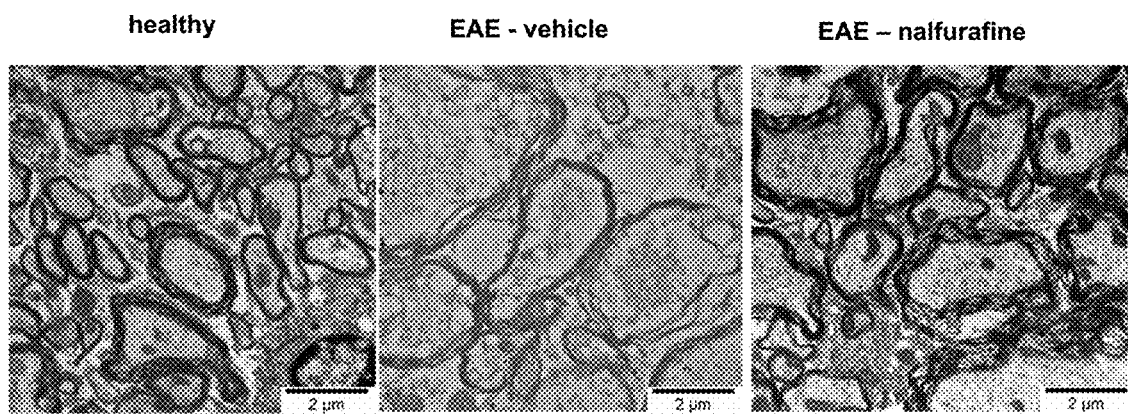

Example 6: Myelination is Improved in Mice Treated With Nalfurafine After the Onset of Paralysis in the EAE Model of MS Experimental detail: EAE was induced in female C57BL/6 mice as described in Example 1. On day 17, mice were started on daily treatment with vehicle only or nalfurafine at 0.03 mg/kg by i.p. injection. On day 45 after immunization to induce EAE, mice were culled, and spinal cords were processed for transmission electron microscopy (TEM). Shown in FIGS. 6A-C are representative TEM images of spinal cord sections from a healthy (A), vehicle-treated EAE (B), or nalfurafine-treated EAE mouse (C) stained to show that dark myelin rings around the nerve axons.

Interpretation and impact: At day 45, there was a significant reduction in the dark stained myelin in the spinal cord of the vehicle-treated EAE mice suggesting demyelination has occurred. Additionally, the nerve axons appear bloated and the cytoplasm disorganized suggesting cellular stress. In contrast, the nerve axons appear healthy and well-myelinated in the nalfurafine-treated mouse, which is concordant with full functional recovery.

Example 7: Nalfurafine Improved Weight Gain When Administered After Demyelination in the Cuprizone Model of Demyelination Experimental detail: Female, C57BL/6 mice were fed 0.3% cuprizone in the diet for 5 weeks to induce demyelination. At the start of week 4 (vertical dashed line in FIG. 7), mice were started on daily treatment with vehicle only or nalfurafine 0.1 mg/kg by i.p. injection. At the start of week 5 (vertical dotted line in FIG. 7), cuprizone was removed from the diet to enable spontaneous remyelination. Mice were weighed daily and the % weight change calculated.

Figure 7:
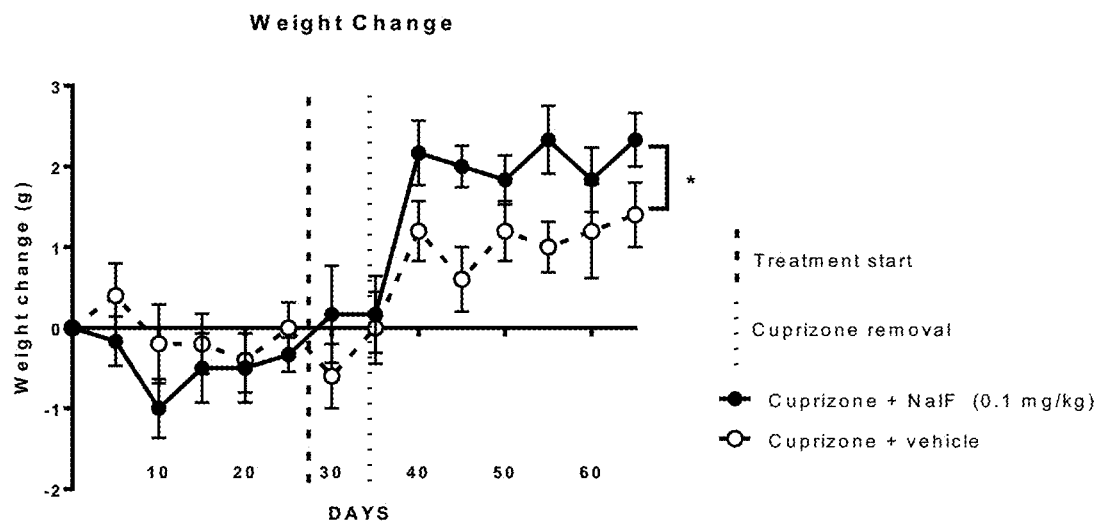

Interpretation and impact: As shown in FIG. 7, cuprizone caused significant weight loss in mice as previously reported. This weight loss was reversed significantly more effectively by administration of nalfurafine than vehicle alone.

Example 8: Nalfurafine Enhances the Functional Recovery of Coordination and Balance When Administered After Demyelination in the Cuprizone Model of Demyelination Experimental detail: Female, C57BL/6 mice were fed 0.3% cuprizone in the diet for 5 weeks to induce demyelination and treated with nalfurafine as described in Example 7. Behavioural tests including the rotarod assay, which measures coordination, were performed weekly. Mice were trained on an accelerating rotarod apparatus (Panlab, Harvard Apparatus) over a period of 4 to 5 days before recording baseline latencies at day 0 followed by weekly measurements throughout cuprizone treatment and recovery. The rotarod was set to 4 rotations per minute (rpm) and an acceleration rate of 40 rpm with a maximum cut-off time of 5 minutes. The time and speed at which the animal falls off the rotating rod was recorded and the average of 3 replicates recorded. Data shows performance at week 9 following Veh or nalfurafine (0.1 mg/kg) treatment relative to performance at week 5. *$p<0.05$ by Students t-test.

Figure 8:
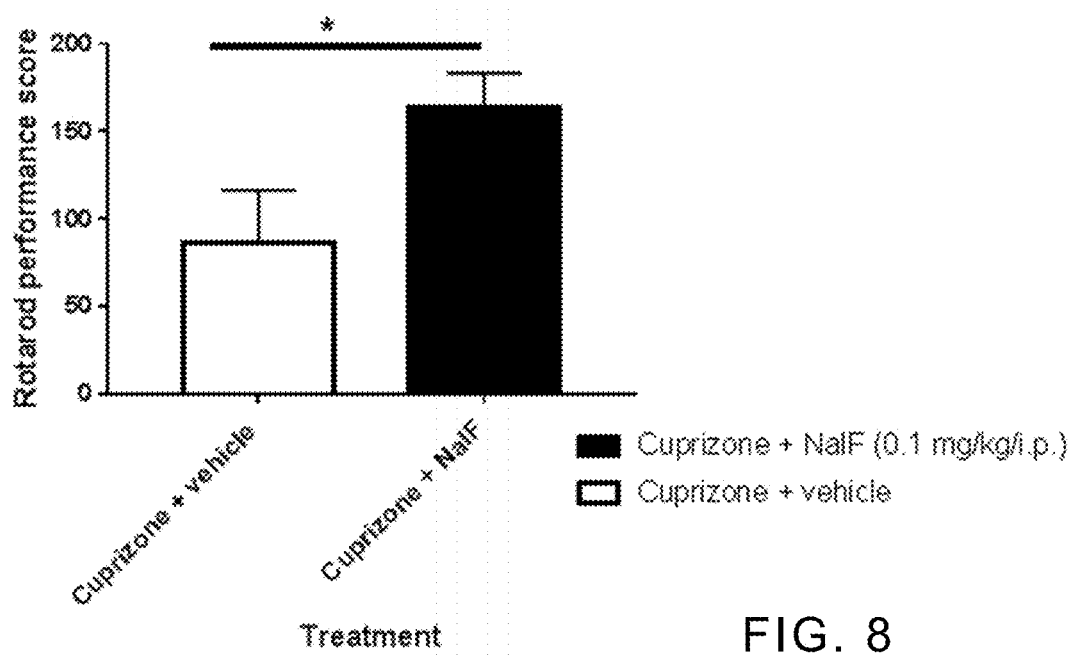

Interpretation and impact: As shown in FIG. 8, cuprizone impaired coordination in mice as previously reported. Cuprizone-induced disability was reversed by administration of nalfurafine. These data suggest that nalfurafine is effective at reducing disability in a model of non-immune mediated demyelination such as that found in some progressive MS patients.

Example 9: Nalfurafine Enhances Myelination When Administered After Demyelination in the Cuprizone Model of Demyelination Experimental detail: Female, C57BL/6 mice were fed 0.3% cuprizone in the diet for 5 weeks to induce demyelination as described in Example 7. On day 65, mice were culled, and brains were processed for transmission electron microscopy (TEM). Shown are representative TEM images of sections from the corpus callosum of a healthy (no cuprizone), vehicle-treated & cuprizone-treated, or nalfurafine-treated & cuprizone-treated mouse stained to show the dark myelin rings around the nerve axons. Myelin was quantified by g-ratio, which is the inner axonal diameter divided by the total outer diameter.

Interpretation and impact: As shown in FIGS. 9A-D, cuprizone caused a loss of myelin and a concurrent disruption in regular axonal structures in the corpus callosum compared to healthy controls. In contrast, more myelin was detected, and the structure was less disorganized in the corpus callosum of animals treated with cuprizone & nalfurafine. These data indicate that nalfurafine treatment promotes remyelination and repair after cuprizone-induced, non-immune-mediated demyelination. A similar non-immune associated demyelination occurs in some progressive MS patients.

Figure 10:
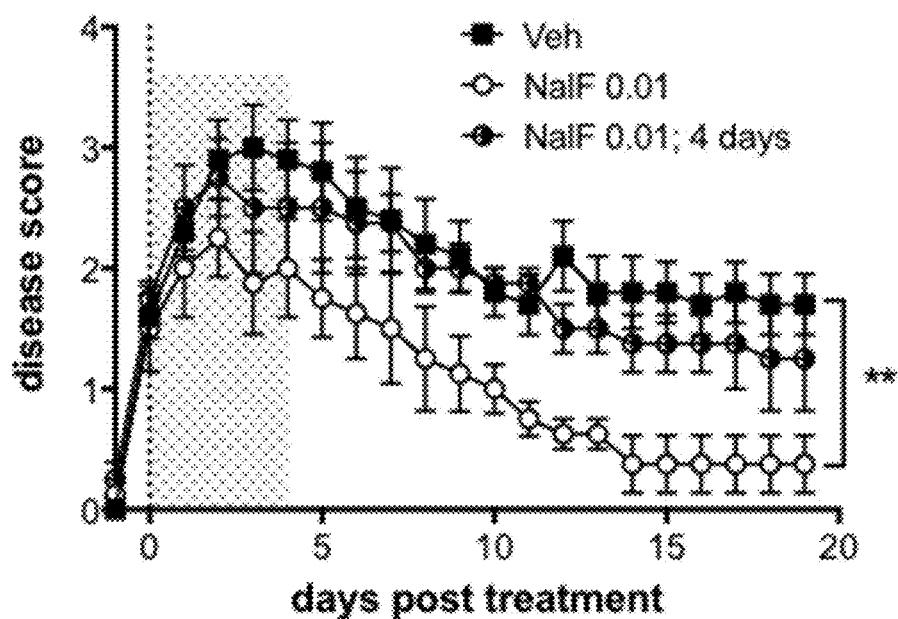
FIG. 10 shows that nalfurafine promotes functional recovery from paralysis when administered therapeutically (at disease onset) in the experimental autoimmune encephalomyelitis (EAE) model of MS.

Example 10: Nalfurafine Promotes Functional Recovery From Paralysis When Administered Therapeutically in the Experimental Autoimmune Encephalomyelitis (EAE) Model of MS Experimental detail: EAE was induced in female C57BL/6 mice as described in Example 1. Results are shown in FIG. 10. On the day of disease onset (score $\geq 1$, dotted line), mice were started on daily treatment with vehicle only (Veh) or nalfurafine at 0.3, 0.1, 0.03, 0.01, or 0.003 mg/kg by i.p. injection. Treatment allocation was blinded. Shown are the aligned scores from mice (n=33 in Veh, 3 in 0.3, 4 in 0.1, 5 in 0.03, 20 in 0.01, and 4 in 0.003 mg/kg groups) starting from onset/treatment initiation. One animal in the 0.3 mg/kg nalfurafine group and 2 from the vehicle group were euthanized at day 17-18. ****$p<0.0001$ by two-way ANOVA all doses (except 0.3 mg/kg) compared to vehicle.

Interpretation and impact: By treating after the onset of disease (paralysis), we show that nalfurafine is able to treat on-going disease. The reduction of disease in all nalfurafine-treated groups indicates recovery from paralysis, which is complete at some doses (0.01 and 0.03 mg/kg); full recovery from disease is unusual in this model and the efficacy of the nalfurafine treatment is surprising. Finally, the dose at which nalfurafine shows the most rapid recovery in this example is 0.01 mg/kg, and this finding has been replicated in 6 independent experiments.

Figure 11:
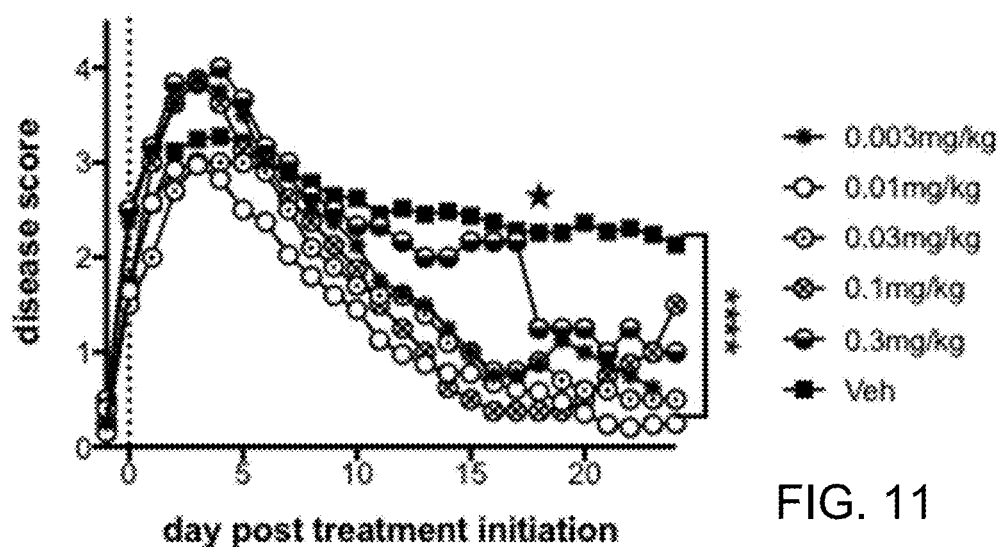
FIG. 11 shows that nalfurafine is not effective when administered therapeutically as a short 4-day course starting at disease onset in EAE model of MS.

Example 11: Nalfurafine is Not Effective When Administered as a Short 4-Day Course Starting at Disease Onset in EAE Model of MS Experimental detail: EAE was induced in female C57BL/6 mice as described in Example 1. Results are shown in FIG. 11. On the day of disease onset (score $\geq 1$, dotted line), mice were started on daily treatment with vehicle only or nalfurafine at 0.01 mg/kg by i.p. injection daily throughout the experimental course or only for four days (shaded area). Shown are the aligned scores from mice (n=5/group) starting from onset/treatment initiation. **$p<0.01$ by two-way ANOVA NaIF (full treatment) compared to nalfurafine (4 days) or vehicle.

Interpretation and impact: Treatment with nalfurafine does not enhance recovery when administered for only four days starting from disease onset, whereas treatment with a longer duration does enhance recovery effectively.

Figure 12:
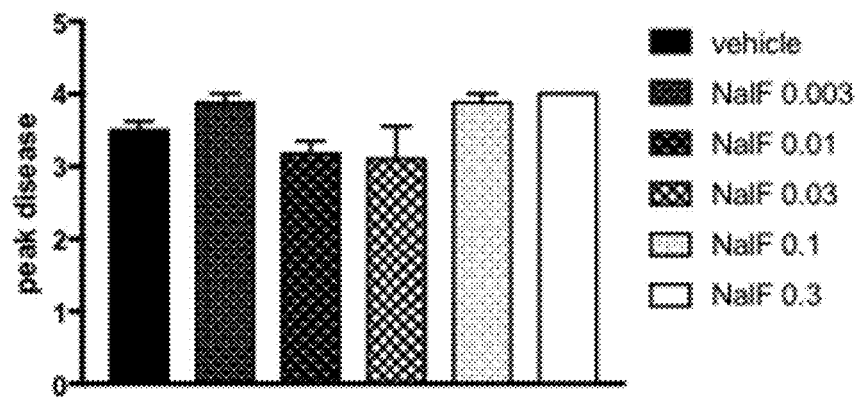
FIG. 12 shows that nalfurafine does not alter peak disease when administered therapeutically in the EAE model of MS.

Example 12: Nalfurafine Does Not Alter Peak Disease When Administered Therapeutically in the EAE Model of MS Experimental detail: EAE was induced in female C57BL/6 mice as described in Example 1. Results are shown in FIG. 12. On the day of disease onset (score ≥1), mice were started on daily treatment with vehicle only or nalfurafine at 0.3, 0.1, 0.03, 0.01, or 0.003 mg/kg by i.p. injection. The peak disease score during the first EAE episode was recorded and shown are the mean and standard error of individual mice (n=33 in Veh, 3 in 0.3, 4 in 0.1, 5 in 0.03, 20 in 0.01, and 4 in 0.003 mg/kg groups). No significant differences were found between any nalfurafine dose and vehicle by Kruskal-Wallis with Dunn's multiple comparison test. These data are from the same experiments as Example 10.

Interpretation and impact: Because no difference in peak disease score was found at any dose of nalfurafine compared to vehicle, nalfurafine did not appear to alter the initial immune-mediated neuroinflammatory event that leads to demyelination and paralysis. This finding suggests that the functional improvement observed (i.e. the recovery from paralysis) occurs because the initial insult has been repaired and perhaps not because the initial insult itself was stopped.

Figure 13:
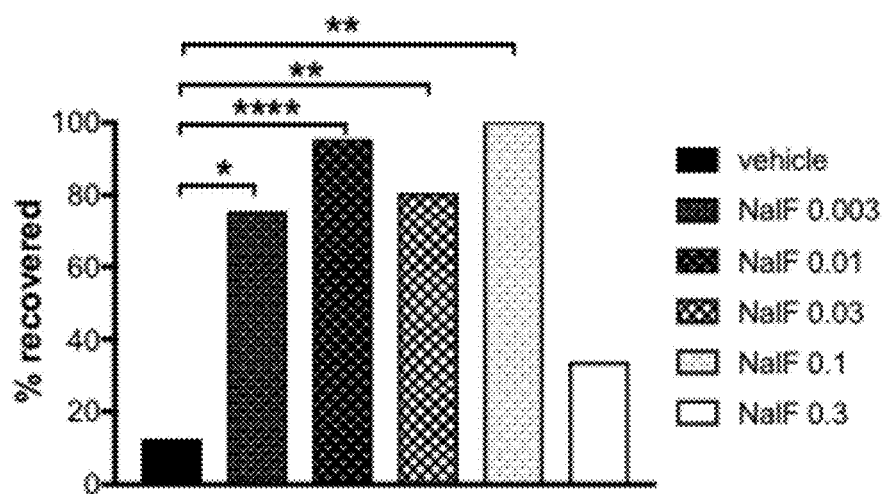
FIG. 13 shows that nalfurafine promotes full recovery from EAE-induced paralysis when administered therapeutically.

Example 13: Nalfurafine Promotes Full Recovery From EAE-Induced Paralysis When Administered Therapeutically Experimental detail: EAE was induced in female C57BL/6 mice as described in Example 1. Results are shown in FIG. 13. On the day of disease onset (score ≥1), mice were started on daily treatment with vehicle only or nalfurafine at 0.3, 0.1, 0.03, 0.01, or 0.003 mg/kg by i.p. injection. Mice were considered recovered if they received a score ≤0.5 by day 23 post treatment initiation. Shown are the percentages of mice in each group that recovered (n =33 in Veh, 3 in 0.3, 4 in 0.1, 5 in 0.03, 20 in 0.01, and 4 in 0.003 mg/kg groups). **p<0.0001, p<0.01, and *p<0.05 by Fisher's exact test. These data are from the same experiments as Example 10.

Interpretation and impact: Treatment with nalfurafine enables full functional recovery (i.e. no paralysis) when administered therapeutically and at a wide range of doses (0.003-0.1 mg/kg all show a significant effect). Full recovery in this model of disease is unusual. The efficacy achieved with the treatment of nalfurafine is extraordinary.

Figure 14:
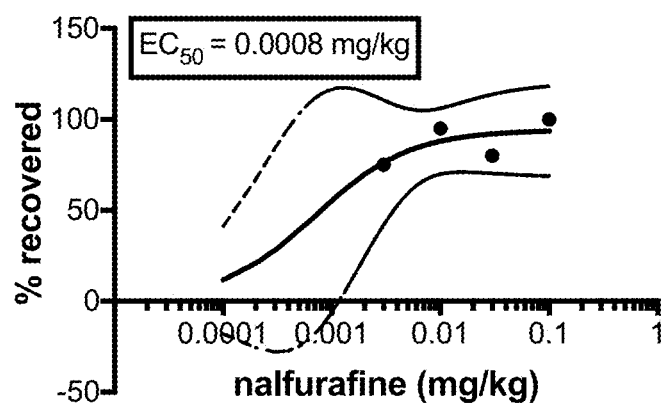
FIG. 14 shows that nalfurafine promotes full recovery from EAE-induced paralysis when administered therapeutically with an EC50 for % recovery of <0.001 mg/kg.

Example 14: Nalfurafine Promotes Full Recovery From EAE-Induced Paralysis When Administered Therapeutically With an $EC_{50}$ of <0.001 mg/kg Experimental detail: EAE was induced in female C57BL/6 mice as described in Example 1. Results are shown in FIG. 14. On the day of disease onset (score ≥1), mice were started on daily treatment with vehicle only or nalfurafine at 0.1, 0.03, 0.01, or 0.003 mg/kg by i.p. injection. Mice were considered recovered if they received a score ≤0.5 by day 23 post treatment initiation. Shown are the percentages of mice in each group that recovered (n=33 in Veh, 4 in 0.1, 5 in 0.03, 20 in 0.01, and 4 in 0.003 mg/kg groups). A dose-response curve has been fitted from a dose of 0.1 mg/kg, in which 100% recovered, to the vehicle alone, in which 12.1% recovered. This curve calculates an $EC_{50}$ of <0.001 mg/kg. These data are from the same experiments as Example 13.

Interpretation and impact: Treatment with Nalfurafine enables full functional recovery (i.e. no paralysis) when administered therapeutically and at a wide range of doses (0.003-0.1 mg/kg all show a significant effect). Full recovery in this model of disease is unusual. The efficacy achieved with the treatment of nalfurafine is extraordinary. To achieve 50% of this effect (i.e. $EC_{50}$) an estimated dose of <0.001 mg/kg is required.

Figure 15:
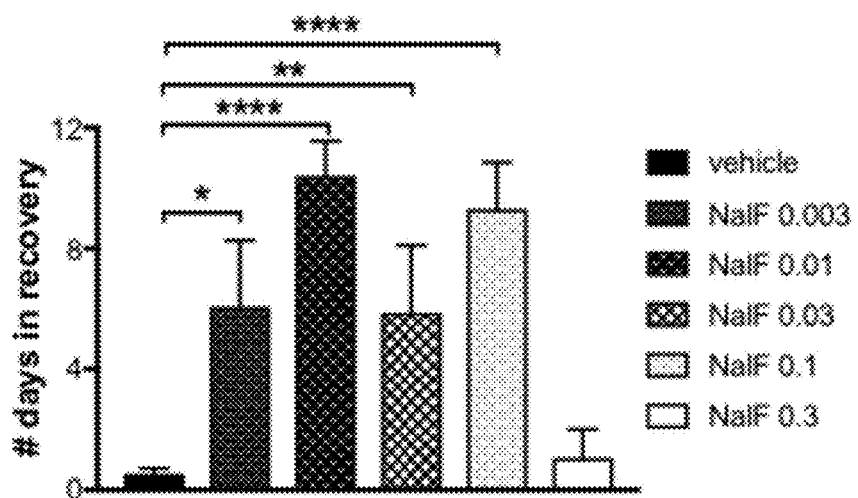
FIG. 15 shows that nalfurafine promotes sustained recovery from EAE-induced paralysis when administered therapeutically.

Example 15: Nalfurafine Promotes Sustained Functional Recovery From EAE-Induced Paralysis When Administered Therapeutically Experimental detail: EAE was induced in female C57BL/6 mice as described in Example 1, Results are shown in FIG. 15. On the day of disease onset (score ≥1), mice were started on daily treatment with vehicle only or nalfurafine at 0.3, 0.1, 0.03, 0.01, or 0.003 mg/kg by i.p. injection. Mice were considered recovered if they received a score ≤0.5 by day 23 post treatment initiation. Shown are the number of days mice were in recovery in each group (n=33 in Veh, 3 in 0.3, 4 in 0.1, 5 in 0.03, 20 in 0.01, and 4 in 0.003 mg/kg groups). **p<0.0001, p<0.01, and *p<0.05 by one-way ANOVA with Holm-Sidak's multiple comparison test. These data are from the same experiments as Example 10.

Interpretation and impact: Treatment with nalfurafine enables a sustained functional recovery (i.e. no paralysis) when administered therapeutically and at a wide range of doses (0.003-0.1 mg/kg all show a significant effect).

Figure 16:
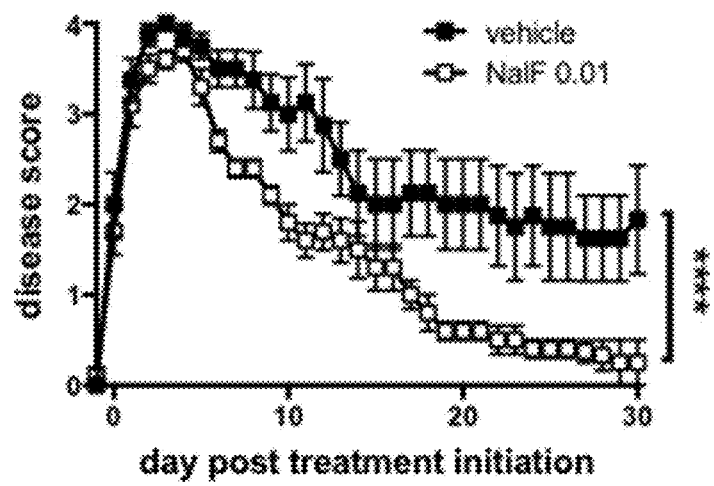
FIG. 16 shows that nalfurafine also promotes functional recovery from paralysis in male mice when administered therapeutically in EAE model of MS.

Example 16: Nalfurafine Promotes Functional Recovery From Paralysis in Male Mice When Administered Therapeutically in EAE Model of MS Experimental detail: EAE was induced in male C57BL/6 mice as described in Example 1. Results are shown in FIG. 16. On the day of disease onset (score ≥1, line), mice were started on daily treatment with vehicle only or nalfurafine at 0.01 mg/kg by i.p. injection. Treatment allocation was blinded. Shown are the aligned scores from mice (n=5/group) starting from onset/treatment initiation. ****p<0.0001 by two-way ANOVA compared to vehicle.

Interpretation and impact: Nalfurafine is effective at enabling functional recovery from paralysis in both females and males.

Figure 17:
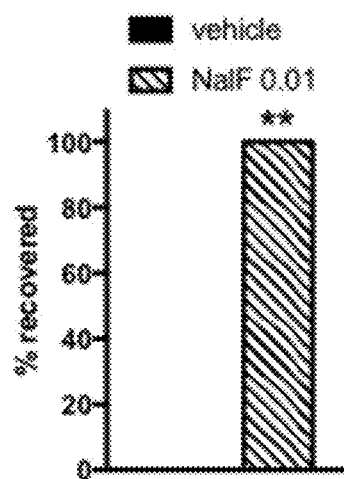
FIG. 17 shows that nalfurafine also promotes full recovery in male mice when administered therapeutically in EAE model of MS.

Example 17: Nalfurafine Promotes Full Recovery in Male Mice When Administered Therapeutically in EAE Model of MS Experimental detail: EAE was induced in male C57BL/6 mice as described in Example 1. Results are shown in FIG. 17. On the day of disease onset (score ≥1), mice were started on daily treatment with vehicle only or nalfurafine at 0.01 mg/kg by i.p. injection. Mice were considered recovered if they received a score ≤0.5 by day 23 post treatment initiation. Shown are the percentages of mice in each group that recovered (n=5/group). **p<0.01 by Fisher's exact test. These data are from the same experiments as Example 16.

Interpretation and impact: Treatment with nalfurafine promotes full recovery (i.e. no paralysis) in both female and male when administered therapeutically.

Figure 18:
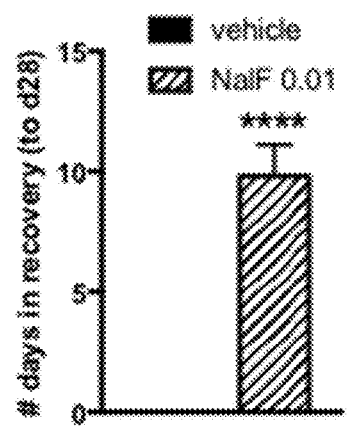
FIG. 18 shows that nalfurafine promotes sustained recovery in male mice from EAE-induced paralysis when administered therapeutically.

Example 18: Nalfurafine Promotes Sustained Recovery in Male Mice From EAE-Induced Paralysis When Administered Therapeutically Experimental detail: EAE was induced in male C57BL/6 mice as described in Example 1. Results are shown in FIG. 18. On the day of disease onset (score ≥1), mice were started on daily treatment with vehicle only or nalfurafine at 0.01 mg/kg by i.p. injection. Mice were considered recovered if they received a score ≤0.5 by day 23 post treatment initiation. Shown are the number of days mice were in recovery in each group (n=5/group). ****p<0.0001 by Student's t test. These data are from the same experiments as Example 16.

Interpretation and impact: Treatment with nalfurafine enables a sustained functional recovery (i.e. no paralysis) in both females and males when administered therapeutically.

Example 19: Nalfurafine Treatment Reduces the Immune Cell Infiltration Into the Brain When Administered Therapeutically in the EAE Model of MS (A) whereas U-50488 Does Not (B)

Experimental detail: EAE was induced in female C57BL/6 mice as described in Example 1. Results are shown in FIGS. 19A and 19B. On the day of disease onset (score ≥1), mice were started on daily treatment with vehicle only or nalfurafine at 0.3, 0.1, 0.03, 0.01, or 0.003 mg/kg by i.p. injection (A). In a separate experiment, mice were similarly treated with vehicle alone or U-50488, a KOR agonist at 1.6 and 5 mg/kg (B). During the chronic phase (>24 days post treatment initiation), mice were culled, and immune cells isolated from the brains. Isolation was by Percoll gradient as described in White et al. 2018. *Scientific Reports.* 8:259. Once isolated, cells were stained with fluorescently labelled antibodies to identify specific immune cell types and analysed by flow cytometry. All infiltrating immune cells were identified by $CD45^{high}$ expression. The relative number of cells is expressed as a ratio to microglia (MG), a brain resident immune cell identified as $CD45^{medium}CD11b^+$. *p <0.05 by one-way ANOVA with Holm-Sidak's multiple comparison test compared to vehicle. NS, not-significant.

Interpretation and impact: In the chronic stage of EAE, there was a significant elevation in immune cells in the brains of vehicle-treated EAE mice compared to healthy animals (A). Treatment with 0.03 and 0.01 mg/kg nalfurafine significantly reduced the number of infiltrating immune cells suggesting that at these doses, nalfurafine can have immunomodulatory properties. Interestingly, while mice treated with 0.1 and 0.003 nalfurafine had similar levels of infiltrating cells as vehicle-treated animals, these mice had no overt signs of disease and had recovered fully from paralysis (FIG. 13). Additionally, nalfurafine but not U-50488 reduced neuroinflammation in this model indicating that not all KOR agonists have this activity (B).

Example 20: Myelination is Improved in Mice Treated With Nalfurafine After the Onset of Paralysis in the EAE Model of MS Experimental detail: EAE was induced in female C57BL/6 mice as described in Example 1. Results are shown in FIG. 20. On the day of disease onset (score ≥1), mice were started on daily treatment with vehicle only or nalfurafine at 0.03 or 0.01 mg/kg by i.p. injection. During the chronic phase (>24 days post treatment initiation), mice were culled, perfused with 4% paraformaldehyde and spinal cords were processed for histology. Sections were stained with luxol fast blue to assess the % area of the spinal cord that is demyelinated (i.e. does not stain with luxol fast blue). % demyelination was assessed using ImageJ. Shown are the means and standard error of individual values from vehicle (n=7) or 0.01 (n=6) and 0.03 (n=4) nalfurafine-treated EAE mice. **p<0.01 by one-way ANOVA with Holm-Sidak's multiple comparison test.

Interpretation and impact: During the chronic phase, when nalfurafine enabled full functional recovery in mice, there was a significant reduction in the percentage of demyelination in the spinal cord of the nalfurafine-treated EAE mice suggesting remyelination may have occurred.

Example 21: Nalfurafine Does Not Alter the Proportion of Major Lymphocyte Populations in the Spleen During the Chronic Phase of EAE Experimental detail: EAE was induced in female C57BL/6 mice as described in Example 1. Results are shown in FIGS. 21A-C. On the day of disease onset (score >1), mice were started on daily treatment with vehicle only or nalfurafine at 0.01 mg/kg by i.p. injection. During the chronic phase (27 days post treatment initiation), mice were culled and their splenocytes assessed by flow cytometry. The percentage of the major lymphocyte populations were identified using CD4 (CD4 T helper cells), CD8 (CD8 cytotoxic T cells), and B220 (B cells), and expressed as % live leukocytes (i.e. CD45+ cells). Shown are the means and standard error of individual mice with n=3 (healthy), 4 (vehicle) and 8. No significant differences were found between vehicle and healthy or nalfurafine by one-way ANOVA with Holm-Sidak's multiple comparison test.

Interpretation and impact: Nalfurafine do not alter the proportion of the major lymphocyte populations in the spleen despite reducing the number of infiltrating immune cells into the central nervous system. The maintenance of normal lymphocyte numbers in the spleen in the nalfurafine treated mice indicates that nalfurafine does not reduce immune cell infiltration into the brain by killing immune cells.

Example 22: Nalfurafine Does Not Alter the Overall Number of CD4 T Helper Cells in the Spleen But Shifts the CD4 T Cells From an Effector to Memory State Being Suggestive of Immune Resolution During the Chronic Phase of EAE Experimental detail: EAE was induced in female C57BL/6 mice as described in Example 1. Results are shown in FIGS. 22A-D. On the day of disease onset (score >1), mice were started on daily treatment with vehicle only or nalfurafine at 0.01 mg/kg by i.p. injection. During the chronic phase (27 days post treatment initiation), mice were culled and their splenocytes assessed by flow cytometry. Naïve CD4 T cells ($CD4^+CD44^-CD62L^{high}$), effector CD4 T cells ($CD4^+CD44^+CD62L^-$), and central memory CD4 T cells ($CD4^+CD44^+CD62L^{high}$) are expressed as % CD4 T cells. "Teff:cm ratio" is the ratio of effector to central memory T cells. Shown are the means and standard error of individual mice with n=3 (healthy), 4 (vehicle) and 8 . **p<0.01 and *p<0.05 by one-way ANOVA with Holm-Sidak's multiple comparison test.

Interpretation and impact: The increased effector to central memory ratio in the vehicle-treated mice with EAE compared to healthy mice indicates an on-going and active immune response mediated by CD4 T cells. The overall number of CD4 T cells was the same between nalfurafine and vehicle treated mice. The reduced ratio in the nalfurafine-treated compared to the vehicle-treated mice indicates a shift toward a memory phenotype which occurs during the resolution phase of the immune response. The shift to a memory state indicates that immune resolution is occurring in nalfurafine-treated mice in a model of MS where disease is driven by an active immune response.

Example 23: Nalfurafine Reduces Disease But Does Not Enable Full Recovery When the Kappa Opioid Receptor (KOR) is Blocked Experimental detail: EAE was induced in female C57BL/6 mice as described in Example 1. Results are shown in FIG. 23. On the day of disease onset (score >1, dotted line), mice were treated with vehicle only (daily), nalfurafine (0.01 mg/kg by i.p. injection daily), the KOR antagonist norBNI (10 mg/kg by i.p. injection weekly), or both nalfurafine and norBNI. Shown are the aligned scores from mice (n=8-9/group) starting from onset/treatment initiation. ****$p<0.0001$ by two-way ANOVA NaIF compared to vehicle or NaIF+noBNI.

Interpretation and impact: Administration of the KOR antagonist, norBNI, abolishes the ability of nalfurafine to enable full recovery from paralysis (i.e. score <0.5), and this finding indicates that the KOR is required for the full effect of nalfurafine. The finding that nalfurafine is effective at reducing disease independently of the KOR (i.e. in the presence of norBNI) indicates that the full mechanism by which nalfurafine exerts its effects is more complex than KOR activation.

Example 24: Activation of the KOR is Required for Full Recovery From Paralysis Mediated by Nalfurafine Experimental detail: EAE was induced in female C57BL/6 mice as described in Example 1. Results are shown in FIGS. 24A-C. On the day of disease onset (score >1, dotted line), mice were treated with vehicle only (daily), nalfurafine (0.01 mg/kg by i.p. injection daily), the KOR antagonist norBNI (10 mg/kg by i.p. injection weekly), or both nalfurafine and norBNI. The peak disease score during the first EAE episode was recorded, and mice were considered recovered if they received a score <0.5 by day 23 post treatment initiation. Shown are the peak disease scores, the percentage of mice in each group that recovered, and the number of days in recovery (n=8-9/group). $p<0.01$ and **$p<0.0001$ by Fisher's exact test (% recovered) or one-way ANOVA with Holm-Sidak's multiple comparison test (# days in recovery). These data are from the same experiments as Example 23.

Interpretation and impact: Administration of the KOR antagonist, norBNI, abolishes the ability of nalfurafine to enable and sustain recovery from paralysis (i.e. score <0.5), and this finding indicates that the KOR is required for the full effect of nalfurafine at promoting full recovery but not disease reduction.

Example 25: Myelination is Improved in Mice Treated With Nalfurafine After the Onset of Paralysis in the EAE Model of MS Experimental detail: EAE was induced in female C57BL/6 mice as described in Example 1. Results are shown in FIGS. 25A-D. On the day of disease onset (score ≥1), mice were started on daily treatment with vehicle only or nalfurafine 0.01 mg/kg by i.p. injection. During the chronic phase (>24 days post treatment initiation), mice were culled, perfused with 4% paraformaldehyde and spinal cords were processed for histology. Sections were stained with luxol fast blue to assess demyelination. The region of interest taken for analysis is shown in 25A. Note the presence of demyelinated regions (lesions) with less luxol fast blue (LFB) staining (myelin) in the ventral horn in EAE mice receiving vehicle (circle—25B) and no demyelinated lesions present in mice treated with nalfurafine (25C). Quantified data is shown in 25D. For each image, 5 randomised regions of the ventral horn of the spinal cord were analysed in ImageJ using mean grey value and integrated pixel density as an indicator of myelin density. Data is from two individual experiments with n=4 (vehicle), n=8 (nalfurafine) EAE mice respectively. Scale bar=50 µm. *$p<0.05$ by students t-test.

Interpretation and impact: EAE disease induces extensive lesions in the spinal cord (see vehicle only (25B), characterised by a loss of myelin and neurodegeneration, demonstrating that EAE is a destructive disease in the CNS. Treatment of this disease state with nalfurafine reduces this lesion load and demyelination, suggesting that treatment restores the spinal cord tissue to a near normal state by remyelination.

Example 26: Nalfurafine Treatment Decreases Cellular Infiltration Into the Spinal Cord When Administered Therapeutically in the EAE model of MS Experimental detail: EAE was induced in female C57BL/6 mice as described in Example 1. Results are shown in FIGS. 26A-C. On the day of disease onset (score >1), mice were started on daily treatment with vehicle only or nalfurafine 0.01 mg/kg by i.p. injection. During the chronic phase (>24 days post treatment initiation), mice were culled, perfused with 4% paraformaldehyde and spinal cords were paraffin embedded for histology. 10 µM coronal sections were stained with Hematoxylin and Eosin (H&E) to assess of leucocyte infiltration, a marker of inflammation within lesions induced in EAE disease. Note the large number of leucocytes present in the ventral horn of vehicle treated EAE mice, than in EAE mice administered nalfurafine. Images were scored by a blinded observer for the level of infiltration on a scale ranging from 0 (no infiltration) to 3 (maximum infiltration). Data is from two individual experiments: n=7 mice (11 sections) for EAE Vehicle; and n=9 mice (13 sections) for EAE mice treated with nalfurafine. Scale bar =50 µm). Students t-test, *$p<0.05$.

Interpretation and impact: EAE disease induces substantial histopathology in the spinal cord. H&E staining of leucocytes is an indicator of lesion severity, with the higher number of infiltrating cells, the more severe the lesion, including demyelination, as shown in the vehicle only panel and by quantification. Treatment with nalfurafine shows a surprising reduction of infiltrating leucocytes, with a near absence of lesions and demyelination indicating that treatment may resolve lesions and/or cause remyelination.

Figures 1, 27A:
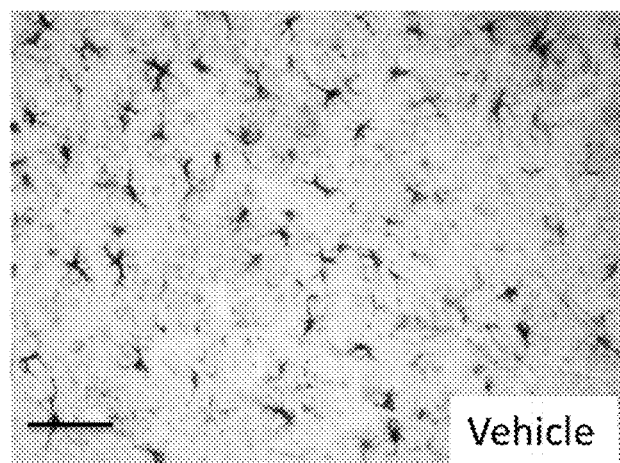
Figures 2, 27A:
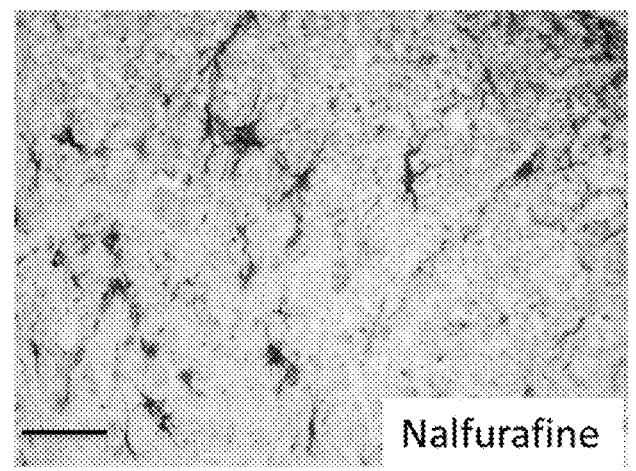
Figure 27B:
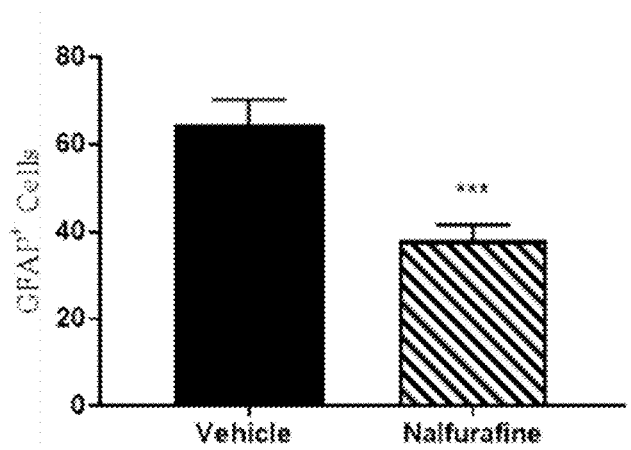

Example 27: Nalfurafine Treatment Reduces the Level of Activated Astrocytes in the Spinal Cord When Administered Therapeutically in the EAE Model of MS Experimental detail: EAE was induced in female C57BL/6 mice as described in Example 1. Results are shown in FIGS. 27A-1, and 27A-2 day 17, mice were started on daily treatment with vehicle only or nalfurafine at 0.01 mg/kg by i.p. injection. On day 45 after immunization to induce EAE, mice were culled, and spinal cords were processed for immunohistochemistry (IHC). Shown in FIGS. 27A-1 and 27A-2 are representative glial fibiliary acid protein (GFAP) immunolabeled cells (black staining) from coronal sections of the ventral horn of the spinal cord taken from EAE mice. The images are from 10 μM paraffin embedded sections, stained with Rabbit anti-GFAP at (1:1000, DAKO) before being photographed at 20× magnification, scale bar=50 μm. The number of astrocytes per section in a standard ROI were counted using the cell counter plug-in in ImageJ. Two sections were assessed per animal. Sections assessed n=7 (10-13 sections, from 2 individual experiment. ***p=0.0003 (FIG. 27B).

Interpretation and impact: As shown and quantified in FIGS. 27A-1 and A-2, at day 45, there was significant elevation in the activated GFAP$^+$ astrocytes in the spinal cord of vehicle treated EAE mice. Astrocytes are recognized to be early and highly active players during lesion formation and key for providing peripheral immune cells access to the central nervous system (Ponath et al. The Role of Astrocytes in Multiple Sclerosis. *Front Immunol.* 2018; 9: 217). Treatment with 0.01 mg/kg i.p. nalfurafine significantly reduces the number of activated astrocytes suggesting that nalfurafine treatment can have a neuroprotective and anti-inflammatory effect on the spinal cord tissue in the disease state (FIG. 27B).

Example 28: Nalfurafine Treatment Enhances Recovery From Weight Loss When Administered Therapeutically in the Cuprizone Demyelination Disease Model of MS FIG. 28A shows a time course of cuprizone induced demyelination and treatment regime.

Experimental details: A demyelinating disease state was induced in female C57BL/6 mice (8-14 weeks old and between 17-23 grams in weight). As shown in the timeline of FIG. 28A, the mice were fed cuprizone-containing chow (0.3% (w/w) cuprizone) or chow only (normal controls) for 35 days, at which point they were switched back to standard chow. At day 28, mice were started on daily treatment with vehicle only (DMSO: Tween 80: Saline) or nalfurafine at 0.1 mg/kg by i.p. injection or U-50488 at 1.6 mg/kg by i.p. injection. On day 70, mice were culled and brain tissue were processed for transmission electron microscopy (TEM). Mice were weighed daily and the % weight change calculated.

Interpretation and impact: This model is well established as a tool for the study of non-immune system induced demyelination. This model enables the assessment of putative remyelination-promoting therapeutics (Matsushima and Morell, 2001. The neurotoxicant, cuprizone, as a model to study demyelination and remyelination in the central nervous system. Brain Pathol. 11, 107-116).

FIG. 28B shows cuprizone induced weight change over the time course of study.

Experimental details: A demyelinating disease state was induced in female C57BL/6 mice as described in Example 28 and illustrated in FIGS. 28A-C.

Interpretation and impact: Mice treated with 0.3% cuprizone (CPZ) lose weight as the disease is induced, compared to mice with normal diet, corresponding to disease induction and severity.

FIG. 28C shows that nalfurafine treatment enhances weight gain in the recovery phase of the cuprizone demyelination disease model of MS, whereas U-50488 does not.

Experimental details: A demyelinating disease state was induced in female C57BL/6 mice as described in FIG. 28C. Diseased animals were treated with Vehicle only, nalfurafine (0.1 mg/kg), U-50488 (1.6 mg/kg) as described in FIG. 28A. Mice were weighed daily and the % weight change calculated. *p<0.05=nalfurafine treated mice; #p<0.05=U-50488 treated mice. Two-way repeated measures ANOVA, followed by Turkey's multiple comparison tests. (n=15 mice/group from 3 experimental replicates. ANOVA revealed a significant interaction $F(40, 600)=2.212$ (p<0.0001) with significant time $F(8, 600)=101.2$ (p<0.0001) and treatment effects $F(5,75)=5.52$ (P<0.0002).

Interpretation and impact: Mice treated with 0.3% cuprizone (CPZ) lose weight as the disease is induced. Mice recover when returned to normal chow (removal of cuprizone) (FIG. 28C). Treatment with nalfurafine enhances recovery of the lost weight faster compared to mice with vehicle only or treatment with U-50488.

Example 29: Nalfurafine Treatment Enhances Remyelination When Administered After Demyelination in the Cuprizone Demyelination Disease Model of MS Experimental details: A demyelinating disease state was induced in female C57BL/6 mice as illustrated in FIG. 28A. The results are shown in FIGS. 29A-G. Panels A-D of FIG. 29 show representative Transmission Electron Microscopy (TEM) images of the corpus callosum of mice (A) fed normal diet and (B-D) fed 0.3% cuprizone to induce demyelination. Following the time course shown in FIG. 28A, cuprizone fed mice were administered (B) vehicle only treatment, (C) U-50488 (1.6 mg/kg/i.p.) and (D) nalfurafine (0.1 mg/kg/i.p.) and then sacrificed on experimental day 70. Scale bars represent 2000 nm.

Figure 29A:
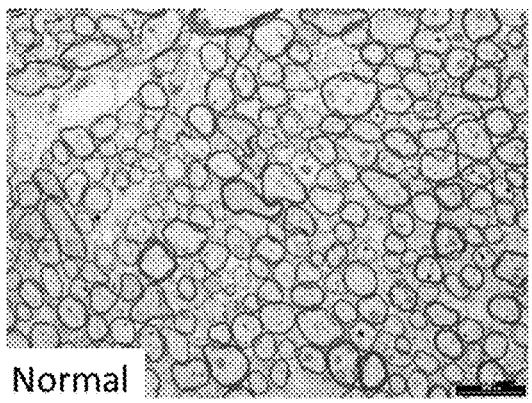
Figure 29B:
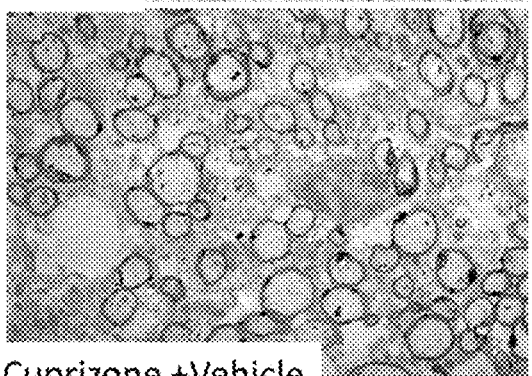
Figure 29C:
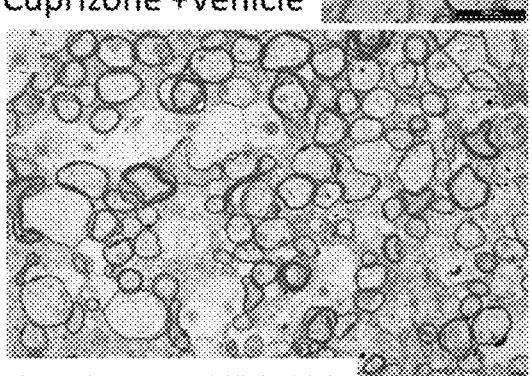
Figure 29D:
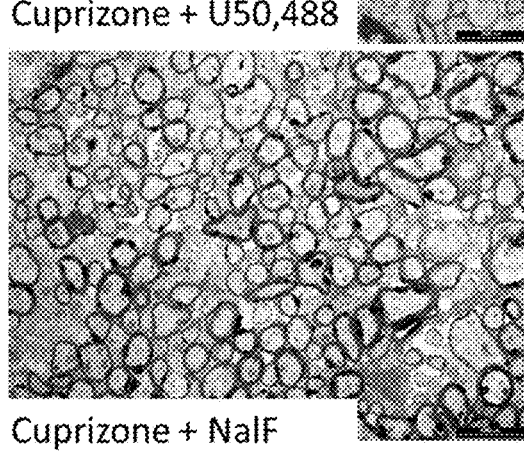
Figure 29E:
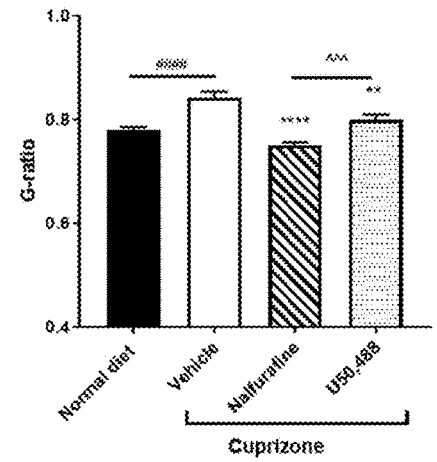

FIG. 29E shows the quantification and analysis of the g-ratios shows a significant difference between treatment groups $F(3,953)=21.18$ (p<0.0001). Mice fed a normal diet have a mean g-ratio of 0.78±0.09 in contrast to mice fed 0.3% cuprizone that have a significant increase in g-ratio of 0.84±0.1 corresponding to the decreased myelin thickness (####p<0.0001). Mice fed a diet with cuprizone treated with nalfurafine (0.1 mg/kg/i.p.) (0.75±0.15) show a significant reduction in g-ratio compared to Vehicle treated controls (**p<0.0001), corresponding to an increased myelin thickness. Mice fed a diet with cuprizone treated with U-50488 show a somewhat increased myelin thickness compared to vehicle-treated controls with a mean g-ratio of (0.80) (p<0.01), but, surprisingly, nalfurafine treatment showed a significant increase in myelin thickness (decrease in g-ratio) compared to mice treated with U-50488 (1.6 mg/kg/i.p.) (^^^p<0.001), indicating that nalfurafine is significantly more effective at increasing myelin thickness than U-50488. Data represents measurements of 5 TEM images of the corpus callosum from two-three mice per treatment group and g-ratios calculated (a measure of myelin thickness) using ImageJ software. Analysis was performed by individuals blinded to treatment groups. (n=204-267 axons per treatment group).

Figure 29F:
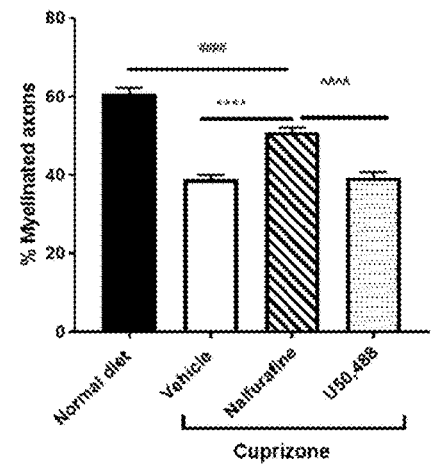

FIG. 29F shows the quantification and analysis of the number of myelinated axons vs non-myelinated axons in a region of interest (390 μm$^2$). n=20 images per treatment group (from n=2-3 mice).

Figure 29G:
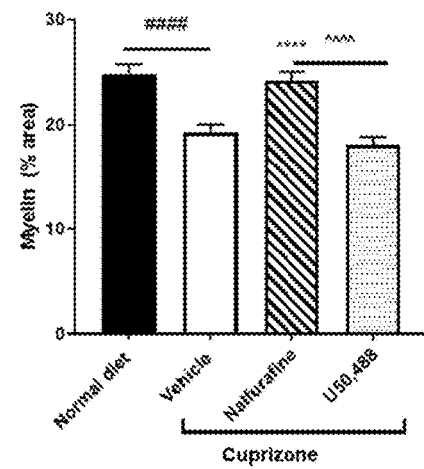
Figures 1, 32A:
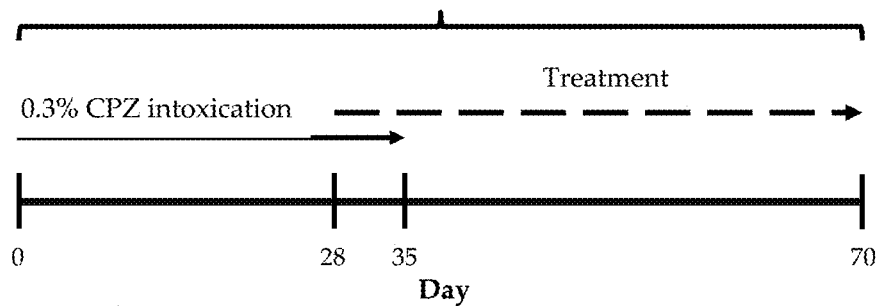
Figures 2, 32A:
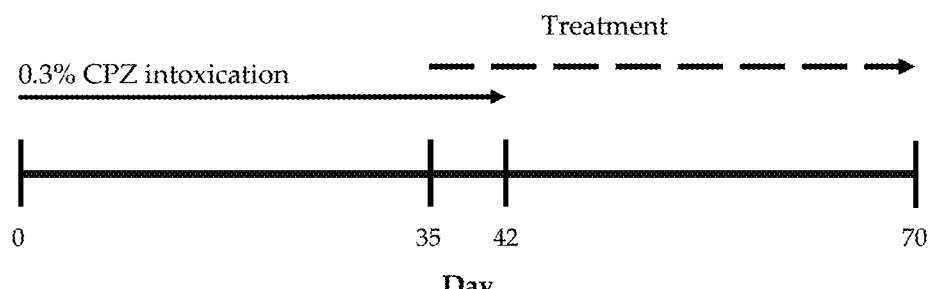
Figure 32B:
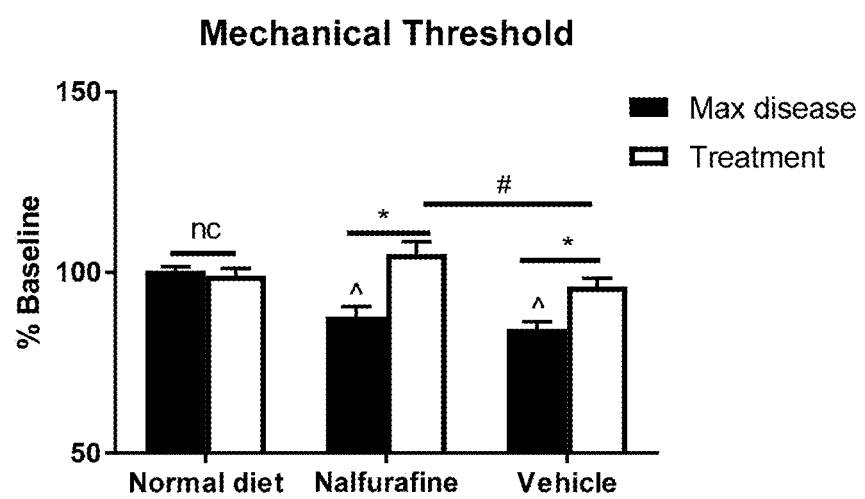

FIG. 29G shows the quantification and analysis of the area of myelin staining per TEM image was performed using ImageJ software (20 images per treatment from n=2-3 mice sacrificed on day 70). TEM images were colour inverted (myelin white) and a threshold used to reveal myelin. The area of this myelin threshold measured for each treatment group.

All data analysed by one-way ANOVA followed by Turkeys multiple comparisons test. Significant differences compared to vehicle only are depicted by *; between normal mice and cuprizone/vehicle treated mice #; and between nalfurafine and U-50488 by ^. (*p<0.05; p<0.01; *p<0.001; ****P<0.0001).

Interpretation and impact: As shown in FIGS. 29A-G, demyelination was very apparent in the corpus collosum of the brain of cuprizone-induced, vehicle only treated animals (Panel B). The ratio between axonal circumference and myelin circumference (g-ratio) decreases with normal myelination. The cuprizone induced animals treated with nalfurafine show a more normal axonal-myelin structure, the myelinated axons are densely packed within white matter and the myelin sheaths of neighboring fibers often directly touch. The staining of the myelin sheaths (black) is more prominent indicating increased remyelination. Ultrastructurally, this nalfurafine tissue is surprisingly similar to that of the naïve (normal) tissue. Quantitatively, the nalfurafine tissue has a significantly lower g-ratio compared to vehicle only treated indicative of enhanced remyelination, with a g-ratio closer to that of naïve (normal) tissue. This is further supported by analysis of the percentage increase in the number of myelinated axons and percentage increase in area of myelination in the nalfurafine treated animals. In contrast, treatment with the compound U-50488 did not show repair or restoration to a near normal state. Qualitatively, the axonal-myelin structure is disorganised, there is a loss of axons, and overtly enlarged axonal-myelin structures. Quantitatively, U-50488 treatment has outcomes similar to that of the vehicle only treated samples (i.e. no discernible remyelination), whereas nalfurafine treatment shows similar outcomes to the naïve tissue. Qualitatively and quantitatively, nalfurafine treatment enhances remyelination that is indicative of a near-full recovery following a demyelination insult of cuprizone.

Example 30: Nalfurafine is More Effective at Promoting Functional Recovery Than Clemastine Fumarate, a Known Remyelinating Drug Experimental detail: EAE was induced in female C57BL/6 mice as described in Example 1. Results are shown in FIGS. 30A-B. On the day of disease onset (score >1, dotted line), mice were treated with vehicle only (daily, n=9)) or nalfurafine (0.01 mg/kg by i.p. injection daily; n=8). In a separate similar experiment, mice were treated with vehicle only (n=5) or clemastine fumarate (10 mg/kg by i.p. injection; n=7). Shown are the aligned scores from mice starting from onset/treatment initiation. ****p<0.0001 by two-way ANOVA NaIF or clemastine compared to vehicle.

Interpretation and impact: Clemastine fumarate, an antihistamine which also antagonizes the muscarinic receptor, has been shown to reduce chronic disability in the EAE model when used at 10 mg/kg starting at the time of immunization. Additionally, it has been shown to enhance remyelination in mice and humans (Li et al. 2015, Clemastine rescues behavioral changes and enhances remyelination in the cuprizone mouse model of demyelination. *Neurosci Bull.;* 31: 617-625; Green, A. J et al., 2017 Clemastine fumarate as a remyelinating therapy for multiple sclerosis (ReBUILD): a randomised, controlled, double-blind, crossover trial. Lancet Lond. Engl. 390, 2481-2489). In our EAE model, clemastine is similarly effective to previously published reports, but is much less effective than nalfurafine at enabling full functional recovery (Mei, F. et al. 2016, Accelerated remyelination during inflammatory demyelination prevents axonal loss and improves functional recovery. ELife 5). This example shows that nalfurafine is superior to clemastine fumarate in this model.

Example 31: Nalfurafine Promotes a Greater and More Sustained Recovery Than Clemastine Fumarate, a Known Remyelinating Drug Experimental detail: EAE was induced in female C57BL/6 mice as described in Example 1. Results are shown in FIGS. 31A-1, 31A-2, 31B-1 and 31B-2. On the day of disease onset (score >1, dotted line), mice were treated with vehicle only (daily, n=9)) or nalfurafine (0.01 mg/kg by i.p. injection daily; n=8)(A). In a separate similar experiment, mice were treated with vehicle only (n=5) or clemastine fumarate (10 mg/kg by i.p. injection; n=7) (B). Mice were considered recovered if they received a score <0.5 by day 23 post treatment initiation. Shown are the percentage of mice in each group that recovered (A) and the number of days in recovery (B). ****p<0.0001 by Fisher's exact test (% recovered; A) or one-way ANOVA with Holm-Sidak's multiple comparison test (# days in recovery; B). These data are from the same experiments as Example 30.

Interpretation and impact: Clemastine fumarate, an antihistamine which also antagonizes the muscarinic receptor, has been shown to reduce chronic disability in the EAE model when used at 10 mg/kg starting at the time of immunization. Additionally, it has been shown to enhance remyelination in mice and humans. In our EAE model, clemastine fumarate treatment promotes recovery in just over 50% of the mice but the recovery is not sustained. In contrast, all of the mice recover when treated with nalfurafine and have a sustained recovery. This finding indicates that nalfurafine is superior to clemastine fumarate in this model and provides a more sustained improvement in every animal treated.

Example 32: Nalfurafine Promotes Recovery in Pain Threshold When Administered After Demyelination in the Cuprizone Demyelination Disease Model of MS Experimental detail: A demyelinating disease state was induced in female C57BL/6 mice (8-14 weeks older and between 17-23 grams in weight). The mice were fed cuprizone-containing chow (0.3% (w/w) cuprizone) or chow only (normal controls) for 35 days, at which point they were switched back to standard chow. At day 28, mice were started on daily treatment with vehicle only (DMSO: Tween 80: Saline) or nalfurafine at 0.1 mg/kg by i.p. injection. In a second experiment, mice were fed cuprizone-containing chow (0.3% (w/w) cuprizone) or chow only (normal controls) for 42 days, at which point they were switched back to standard chow. At day 35, mice were started on daily treatment with vehicle only (DMSO: Tween 80: Saline) or nalfurafine at 0.1 mg/kg by i.p. injection. In both studies, on day 70, mice were culled. See FIG. 32A for an outline of the disease induction and treatment time course.

Sensitivity to mechanical force elicits paw withdrawal in mice. Threshold to withdrawal is measured using calibrated von Frey filaments using the up-down method (Bonin et al. A simplified up-down method (SUDO) for measuring mechanical nociception in rodents using von Frey filaments. Molecular Pain. 2014; 10:1-11) at maximum disease, prior to treatment with nalfurafine. Cuprizone causes increased mechanical sensitivity compared to mice on a normal diet (^p<0.05) (FIG. 32B), and this increase in mechanical withdrawal threshold is reduced to baseline levels following treatment with nalfurafine (0.1 mg/kg/i.p.). *p<0.05 at maximum disease (day 28 or 35) and following daily treatment with nalfurafine (average threshold days 45-70). Nalfurafine treated mice improved mechanical threshold scores compared to vehicle treated mice(#p<0.05). Student t-test, n=10-11 mice/group from 2 independent experiments. ^ compared to mice on normal diet; * threshold pre and post treatment; # differences in recovery between treatment groups. Pooled data from 2 experimental cohorts were analysed (max disease is week prior to treatment initiation and at maximal recovery (days 63-70).

Interpretation and impact: Chronic pain is often associated with multiple sclerosis. Allodynia is an increase in pain sensation to a normally non-painful stimulus. In this test von Frey filaments are used to measure the paw withdrawal threshold following application of a defined mechanical force. Following cuprizone induced demyelination, the pain threshold is a functional biomarker for recovery, indicative of remyelination of the nerve fibres. Remarkably, the diseased animals treated with nalfurafine showed a pain sensitivity that was similar to baseline, indicating that treatment enhances functional recovery.

The invention claimed is:

1. A method of treating a demyelinating disease in a subject, the method comprising administering a pharmaceutical composition comprising a therapeutically effective amount of about 0.1 µg to about 250.0 µg of nalfurafine to the subject on a daily basis for a period of at least 7 days, wherein the therapeutically effective amount of nalfurafine is sufficient to increase remyelination in the human subject.

2. The method according to claim 1, wherein the pharmaceutical composition is administered to the subject to obtain a dosage of about 0.1 to about 10.0 µg nalfurafine daily.

3. The method according to claim 1, wherein the demyelinating disease is selected from the group consisting of multiple sclerosis (MS), optic neuritis, Devic's disease, inflammatory demyelinating diseases, central nervous system neuropathies, myelopathies, Tabes dorsalis, leukoencephalopathies, leukodystrophies, Guillain-Barre syndrome and its chronic counterpart, chronic inflammatory demyelinating polyneuropathy, anti-MAG (myelin-associated glycoprotein) peripheral neuropathy, Charcot Marie Tooth (CMT) disease, copper deficiency, progressive inflammatory neuropathy, and any combination thereof.

4. The method according to claim 1, wherein administration of the pharmaceutical composition to the subject results in one or more clinical outcomes selected from the group consisting of:
 a decrease or delay in nerve cell demyelination;
 a healing of damaged nerve tissue;
 an increase in remyelination of demyelinated nerves in the subject's central nervous system;
 neuroprotection;
 protection of damaged nerve tissue from further disease activity;
 promotion of neuronal outgrowth in the subject's central nervous system;
 an improvement in nerve function;
 a decrease in demyelinating disease progression;
 a decrease in demyelinating disease severity;
 a decrease in frequency or severity of relapsing demyelinating disease attacks;
 a decrease in disability caused by demyelinating disease;
 a decrease in demyelinating disease clinical symptoms;
 a decrease in paralysis;
 an improvement in balance or coordination; and
 an enhanced rate of remission.

5. The method according to claim 1, wherein administration of the pharmaceutical composition to the subject results in a reduction of one or more clinical symptoms selected from the group consisting of: loss of sensitivity, muscle weakness, impaired walking, impaired hand function, pronounced reflexes, muscle spasms, difficulty in moving, ataxia, spasticity, problems with speech or swallowing, visual problems, fatigue, acute or chronic pain, facial pain, incontinence, reduced cognitive ability, depression, anxiety, sexual dysfunction, Uhthoff's phenomenon, and Lhermitte's sign.

6. A method of increasing remyelination of nerves in a subject, the method comprising administering a pharmaceutical composition comprising a therapeutically effective amount of about 0.1 µg to about 250.0 µg of nalfurafine to the subject on a daily basis for a period of at least 7 days, wherein the therapeutically effective amount of nalfurafine is sufficient to increase remyelination of nerves in the human subject or to improve nerve function, or both.

7. The method according to claim 6, wherein the pharmaceutical composition is administered to the subject to obtain a dosage of about 0.1 to about 10.0 µg nalfurafine daily.

8. The method according to claim 6, wherein the subject has one or more symptoms of a demyelinating disease selected from the group consisting of multiple sclerosis (MS), optic neuritis, Devic's disease, inflammatory demyelinating diseases, central nervous system neuropathies, myelopathies, Tabes dorsalis, leukoencephalopathies, leukodystrophies, Guillain-Barre syndrome and its chronic counterpart, chronic inflammatory demyelinating polyneuropathy, anti-MAG (myelin-associated glycoprotein) peripheral neuropathy, Charcot Marie Tooth (CMT) disease, copper deficiency, progressive inflammatory neuropathy, and any combination thereof.

9. The method according to claim 6, wherein administration of the pharmaceutical composition to the subject results in one or more clinical outcomes selected from the group consisting of:
 a decrease or delay in nerve cell demyelination;
 a healing of damaged nerve tissue;
 an increase in remyelination of demyelinated nerves in the subject's central nervous system;
 neuroprotection;
 protection of damaged nerve tissue from further disease activity;
 promotion of neuronal outgrowth in the subject's central nervous system;
 an improvement in nerve function;
 a decrease in demyelinating disease progression;
 a decrease in demyelinating disease severity;
 a decrease in frequency or severity of relapsing demyelinating disease attacks;
 a decrease in disability caused by demyelinating disease;
 a decrease in demyelinating disease clinical symptoms;
 a decrease in paralysis;
 an improvement in balance or coordination; and
 an enhanced rate of remission.

10. The method according to claim 6, wherein administration of the pharmaceutical composition to the subject results in a reduction of one or more clinical symptoms selected from the group consisting of: loss of sensitivity, muscle weakness, impaired walking, impaired hand function, pronounced reflexes, muscle spasms, difficulty in moving, ataxia, spasticity, problems with speech or swallowing, visual problems, fatigue, acute or chronic pain, facial pain, incontinence, reduced cognitive ability, depression, anxiety, sexual dysfunction, Uhthoff's phenomenon, and Lhermitte's sign.

11. A method of attenuating demyelination of nerves in a subject, the method comprising administering a pharmaceutical composition comprising a therapeutically effective amount of about 0.1 μg to about 250.0 μg of nalfurafine to the subject on a daily basis for a period of at least 7 days, wherein the therapeutically effective amount of nalfurafine is sufficient to decrease demyelination of nerves in the human subject or to attenuate loss of nerve function, or both.

12. The method according to claim 11, wherein the pharmaceutical composition is administered to a mammalian subject to obtain a dosage of about 0.1 to about 10.0 μg nalfurafine daily or wherein the pharmaceutical composition is administered to the mammalian subject to obtain a dosage of nalfurafine which is equivalent to a dose of about 0.003 to about 0.3 mg/kg of nalfurafine in mice.

13. The method according to claim 11, wherein the subject has one or more symptoms of a demyelinating disease selected from the group consisting of multiple sclerosis (MS), optic neuritis, Devic's disease, inflammatory demyelinating diseases, central nervous system neuropathies, myelopathies, Tabes dorsalis, leukoencephalopathies, leukodystrophies, Guillain-Barre syndrome and its chronic counterpart, chronic inflammatory demyelinating polyneuropathy, anti-MAG (myelin-associated glycoprotein) peripheral neuropathy, Charcot Marie Tooth (CMT) disease, copper deficiency, progressive inflammatory neuropathy, and any combination thereof.

14. The method according to claim 11, wherein administration of the pharmaceutical composition to the subject results in one or more clinical outcomes selected from the group consisting of:
 a decrease or delay in nerve cell demyelination;
 a healing of damaged nerve tissue;
 an increase in remyelination of demyelinated nerves in the subject's central nervous system;
 neuroprotection;
 protection of damaged nerve tissue from further disease activity;
 promotion of neuronal outgrowth in the subject's central nervous system;
 an improvement in nerve function;
 a decrease in demyelinating disease progression;
 a decrease in demyelinating disease severity;
 a decrease in frequency or severity of relapsing demyelinating disease attacks;
 a decrease in disability caused by demyelinating disease;
 a decrease in demyelinating disease clinical symptoms;
 a decrease in paralysis;
 an improvement in balance or coordination; and
 an enhanced rate of remission.

15. The method according to claim 11, wherein administration of the pharmaceutical composition to the subject results in a reduction of one or more clinical symptoms selected from the group consisting of: loss of sensitivity, muscle weakness, impaired walking, impaired hand function, pronounced reflexes, muscle spasms, difficulty in moving, ataxia, spasticity, problems with speech or swallowing, visual problems, fatigue, acute or chronic pain, facial pain, incontinence, reduced cognitive ability, depression, anxiety, sexual dysfunction, Uhthoff's phenomenon, and Lhermitte's sign.

* * * * *